United States Patent
McNannay et al.

(10) Patent No.: US 11,021,306 B2
(45) Date of Patent: Jun. 1, 2021

(54) ENHANCED PRODUCT PACKAGING

(71) Applicant: Curadite, Inc., Beaverton, OR (US)

(72) Inventors: Dennis Michael McNannay, Beaverton, OR (US); Dewey Nigma, Jr., Beaverton, OR (US); William Carroll, Beaverton, OR (US); Steven D. Baker, Beaverton, OR (US)

(73) Assignee: CURADITE, INC., Beaverton, OR (US)

( * ) Notice: Subject to any disclaimer, the term of this patent is extended or adjusted under 35 U.S.C. 154(b) by 0 days.

(21) Appl. No.: 16/847,033

(22) Filed: Apr. 13, 2020

(65) Prior Publication Data
US 2020/0361685 A1 Nov. 19, 2020

Related U.S. Application Data

(63) Continuation of application No. 16/515,976, filed on Jul. 18, 2019, now Pat. No. 10,618,714.

(Continued)

(51) Int. Cl.
| | |
|---|---|
| *B65D 75/36* | (2006.01) |
| *H05K 1/02* | (2006.01) |
| *H05K 1/18* | (2006.01) |
| *H04W 4/80* | (2018.01) |
| *H04B 5/00* | (2006.01) |

(52) U.S. Cl.
CPC ......... *B65D 75/367* (2013.01); *H04B 5/0062* (2013.01); *H04W 4/80* (2018.02); *H05K 1/0269* (2013.01); *H05K 1/18* (2013.01); *B65D 2203/10* (2013.01); *H05K 2201/09918* (2013.01);

(Continued)

(58) Field of Classification Search
CPC ........ A61J 1/035; A61J 1/065; A61J 2205/60; B65D 2203/10; B65D 75/367; G16H 20/13; H04B 5/0062; H04W 4/38; H04W 4/70; H04W 4/80; H05K 1/0269; H05K 1/16; H05K 1/18; H05K 2201/09918; H05K 2201/0999; H05K 2201/10037; H05K 2201/10098; H05K 2201/10151
See application file for complete search history.

(56) References Cited

U.S. PATENT DOCUMENTS

2002/0017996 A1* 2/2002 Niemiec ............... A61J 7/0481
340/573.1
2007/0246396 A1* 10/2007 Brollier ................. A61J 7/0481
206/534

(Continued)

*Primary Examiner* — David Bilodeau
(74) *Attorney, Agent, or Firm* — Alleman Hall Creasman & Tuttle LLP

(57) ABSTRACT

A packaging system comprises: a package forming a set of discrete compartments; and a film portion interfacing with the package. The film portion includes a set of one or more electrically conductive traces in which each electrically conductive trace is associated with a respective compartment of the set of discrete compartments. Each electrically conductive trace of the set of electrically conductive traces forms a respective circuit loop that has a terminal end that terminates within an interface region of the film portion to collectively form a termination pattern. At least one of the package or the film portion have two or more alignment ports defined therein that are arranged according to an alignment pattern, each alignment port passing through at least one of the package or film portion.

20 Claims, 11 Drawing Sheets

Related U.S. Application Data

(60) Provisional application No. 62/700,139, filed on Jul. 18, 2018.

(52) U.S. Cl.
    CPC .............. *H05K 2201/10098* (2013.01); *H05K 2201/10151* (2013.01)

(56) References Cited

U.S. PATENT DOCUMENTS

| | | | | |
|---|---|---|---|---|
| 2008/0197043 | A1* | 8/2008 | Freeze | A61J 7/0481 206/538 |
| 2009/0184023 | A1* | 7/2009 | Brollier | A61J 7/0481 206/531 |
| 2009/0194452 | A1* | 8/2009 | Hession | A61J 1/035 206/531 |
| 2011/0155602 | A1* | 6/2011 | Sterry | A61J 7/0436 206/459.1 |
| 2013/0320020 | A1* | 12/2013 | Elliott | A61J 1/035 220/378 |
| 2015/0352010 | A1* | 12/2015 | Simpson | B65D 75/54 206/534 |
| 2016/0103085 | A1* | 4/2016 | Mehregany | A61J 1/035 324/71.1 |
| 2016/0143807 | A1* | 5/2016 | Ika | A61J 1/03 206/216 |
| 2017/0248401 | A1* | 8/2017 | Isom | A61J 7/0481 |

* cited by examiner

ENHANCED PRODUCT PACKAGING

CROSS REFERENCE TO RELATED APPLICATIONS

The present application is a continuation application that claims the benefit of and priority to U.S. patent application Ser. No. 16/515,976, titled ENHANCED PRODUCT PACKAGING, filed Jul. 18, 2019, and issuing as U.S. Pat. No. 10,618,714 on Apr. 14, 2020 which is a non-provisional patent application that claims the benefit of and priority to U.S. provisional patent application No. 62/700,139, filed Jul. 18, 2018, titled "ENHANCED PRODUCT PACKAGING", the entire contents of which are incorporated herein by reference for all purposes.

BACKGROUND

Medications are commonly distributed in packaging such as blister packs. Each compartment of a blister pack is initially sealed by a cover that may be broken or removed to access the medication contained therein. Medications are often assigned to individual compartments in pre-defined quantity, size, or concentration to enable the selection of the appropriate dosage on a per-compartment basis.

SUMMARY

According to an example of the present disclosure, a packaging system comprises: a package forming a set of discrete compartments; and a film portion interfacing with the package, the film portion including a set of one or more electrically conductive traces in which each electrically conductive trace is associated with a respective compartment of the set of discrete compartments. Each electrically conductive trace of the set of electrically conductive traces forms a respective circuit loop that has a terminal end that terminates within an interface region of the film portion to collectively form a termination pattern. At least one of the package or the film portion have two or more alignment ports defined therein that are arranged according to an alignment pattern, each alignment port passing through at least one of the package or film portion. The packaging system may further comprise a communication module that interfaces with the package and/or film portion, including: a module body having two or more alignment posts arranged according to the alignment pattern in which each alignment post passes through an alignment port; and electronic components mounted to the module body. The electronic components include a set of electrical contacts arranged in a contact pattern in which the termination pattern corresponds to at least a portion of the contact pattern of the set of electrical contacts so that each terminal end of the termination pattern interfaces with a corresponding electrical contact of the communication module. The electronic components further include a wireless transmitter, and a logic subsystem programmed with instructions executable by the logic subsystem to: measure, via electrical contacts interfacing with the terminal ends, an electrical property of each electrically conductive trace that is associated with each compartment of the set of discrete compartments to determine an compartment state of that compartment, and transmit wireless communications indicating the compartment state of each compartment of the set of discrete compartments to a remote wireless receiver.

According to another example of the present disclosure, a packaging system comprises: a package including a set of multiple package portions that each form a discrete compartment, the multiple package portions joining each other and being separable from each other along one or more boundaries; a film portion interfacing with the package and spanning the one or more boundaries; and a communication module mounted to at least one of the package or the film portion, and including a logic subsystem and a wireless transmitter. The film portion includes a set of one or more electrically conductive traces that each span a respective boundary of the one or more boundaries. Each electrically conductive trace of the set of electrically conductive traces forms a respective circuit loop that has a terminal end of the circuit loop that terminates at the communication module. The logic subsystem is programmed with instructions executable by the logic subsystem to: measure, via the terminal ends of the set of electrically conductive traces, an electrical property of each electrically conductive trace to determine a state of each boundary of the one or more boundaries, and transmit, via the wireless transmitter, communications to a remote wireless receiver indicating the state of each boundary of the one or more boundaries.

DETAILED DESCRIPTION

Figure 1:
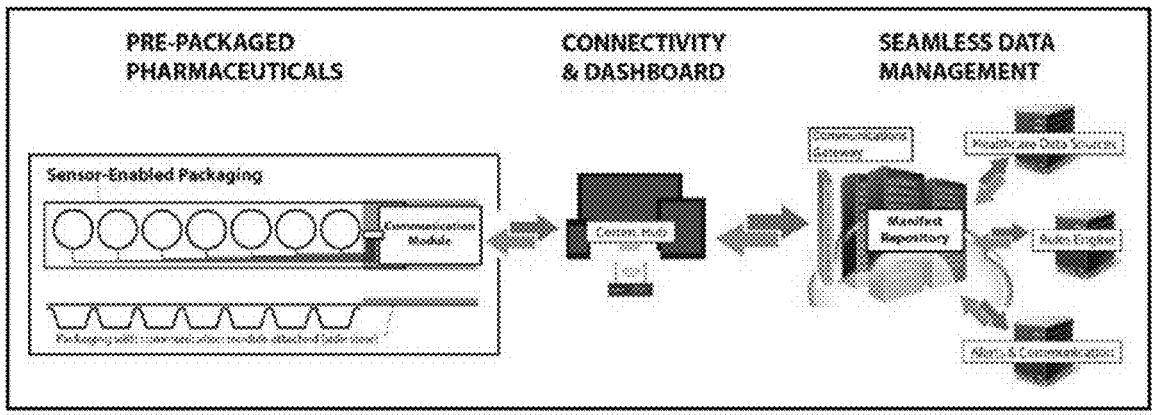
FIG. 1 depicts an exemplary embodiment of the one-time use sensor-enabled packaging system and the other system elements required to support the distribution of monitored packages.

Systems, devices, and methods are disclosed herein for managing and monitoring the delivery, consumption and recycling/disposal of packaged goods through use of smart, connected packaging systems; cloud servers; electronic manifest; and electronic interfaces. The packaging management system comprises a configurable packaging system that has one or more individual sensor-enabled openings corresponding with individual packaging storage compartments; a digital packaging manifest describing the contents of each monitored compartment contained within the packaging system and rules by which they should be consumed; a system to granularly identify, manage and monitor the packaging compartment's contents; a digital repository capable of creating, scheduling, routing and recording two-way communication to and from the user; and mechanisms to analyze and visualize usage and consumption information regarding the status of the package's unique contents described in the packaging content manifest.

Monitoring the use of packaged goods after they are delivered to the end-user can substantially improve a product's usefulness, effectiveness, safety, and convenience. The pharmaceutical industry, for example, has spent decades trying to deploy systems that would provide an inexpensive, flexible, safe and easy-to-use system for helping patients, caregivers and institutions better manage their complex medication regimes, measure potential effectiveness and facilitate the proper disposal of unused drugs. With the average elderly patient consuming over six different prescriptions daily, many of which have interactions with one another, the need for an intuitive, flexible and cohesive packaging solution is clear.

Whether the use case scenario involves patients enrolled in clinical trials, elderly patients taking a complex regimen of drugs to treat chronic medical conditions, children requiring medications administered at schools, or patients recovering from episodic medical procedures (surgeries, infections, etc.), medication adherence is often the difference between a successful medical outcome and an expensive medical re-admittance to the hospital or a premature journey to a life of assisted living. Previous packaging innovations have taught that the most effective solutions must strike a balance between flexibility, technical sophistication and scalability.

Despite numerous unsuccessful attempts to build packaging solutions and mechanized, individual dosage-based dispensing technologies, a large percentage of today's patients still rely on the simple, plastic, dated pill box. This might be because the latest generation of internet enabled pillbox solutions suffer from several significant drawbacks. As reusable technologies, they introduce the risk of mechanical failure and require patients, or their caregivers, to learn new technologies, respond to confusing prompts, or retrofit expensive technologies into their homes. These existing, non-disposable packaging systems also cannot be deployed remotely and must be refilled and maintained by the user or his caregiver. Given today's geographically distributed society, reliance on packaging systems that require regular maintenance support, contents restocking by caregivers or monitoring by local relatives is not realistic.

By using a disposable, sensor enabled packaging system that allows virtually anyone to purchase, provision, deploy, monitor, manage, resupply and dispose of unused contents within an end-to-end monitored system based on existing technology networks and devices, our invention substantially broadens the potential use-case scenarios that can be supported. This innovative new packaging system represents a new philosophical approach to monitoring the usage of packaged goods like pharmaceuticals, nutritional substitutes, and other patient managed treatments as well as providing inventory control of medical equipment such as multi-component orthopedic joints or implant sets.

The use of a broad range of devices may also be mandated, monitored and tracked. For example, when a defibrillator has been added as a data point to be monitored, various parameters can be recorded and verified. This data may be used to determine whether the defibrillator has been serviced according to the service guidelines or to record when/if it was used on a patient. Other non-limiting examples of equipment might include identifying events such as: Filter cleaning, battery replacement, Blood-pressure pump calibration, temperature alerts, etc.

Given the persistence of some pharmaceuticals, and the environmental and social impact of unused drugs being misappropriated for illegal sale or disposal, managing the full product life cycle has also become increasingly important. Alameda County in California has already highlighted these concerns by implementing a first-of-its kind regulation to mandate the environmentally-safe recycling of pharmaceutical products. A trend towards similar national legislation would soon require packaging systems that provide a scalable, reliable system to track prescription drugs through their entire lifecycle—including an environmentally-safe product disposal system.

In the case of pharmaceutical packaging, new packaging solutions must preserve the provenance of their contents in order to also support product recalls and future Track and Trace and Drug Take-back regulatory requirements. Recent events have proven that the ability to track drugs from their manufacturing source, by lot numbers, to individual, distributed doses would significantly improve the safety of our health system. Recent federal legislation to mandate track and trace inventory control systems can only be extended to the end consumer by adopting technologies that maintain the chain of custody to include the final distribution of the individual dosages distributed to the end user or caregiver of a care facility.

Various attempts have been made to address some of the problems associated with drug compliance. For example, some proposed systems attempt to track the dosages taken by a patient so that a determination can be made as to whether the patient is complying with a particular drug regime. Such systems, however, are relatively expensive, complex to operate or set-up, and/or rely too heavily on patient compliance and/or manual or semi-automatic data entry.

Simpler, disposable and more automated systems and methods for monitoring the usage of packaged goods are needed. Medication adherence is a specific usage example where this sensor-enabled packaging invention can yield dramatic societal, corporate and personal benefits.

The present disclosure generally pertains to systems and methods for monitoring the delivery, consumption and recycling of packaged goods. A product management system in accordance with one exemplary embodiment of the present disclosure comprises a non-reusable sensor enabled packaging system that has an array of sensors whereby each sensor is associated with individual packaging storage compartments or sub-packages, a system of unique digital and or physical (e.g. printed description of contents or other relevant data—directions, warnings, etc.) identifiers to granularly identify, monitor and manage the packaging compartment contents, a remotely managed digital packaging manifest describing the contents and rules governing the usage of each available compartment or sub-package within the packaging system, and mechanisms to communicate usage and consumption information regarding the status of the package's unique set of contents described in the digital packaging content manifest and stored in a remote digital manifest repository. In an alternative embodiment, the manifest and rule set governing the usage of the contents of a package may be stored locally within the communication module's resident processor.

Each manifest stored in the manifest repository is used, in conjunction with its usage rules, to track and analyze usage events generated as the user consumes the packaged contents; as a result of the user's actions, the system formulates reminders, notifications, responses and data access requests. The system is also designed to trigger other activities or events on the part of the package recipient, approved trusted technology partners or the activities of other devices, digital processes, or scheduled events. Because the manifest and usage rules are related, they may be called out as one object in this specification; however, the manifest and usage rules can reside in different files and different locations.

In this embodiment of the invention, we define a "communications hub" to be a device that allows the smart-packages communication module (aka sensor-enabled packaging communication module) to gain access to a network such as a wide area network (WAN). Typically, the server that hosts the manifest repository, rules engine, notifications & communication algorithm, and interfaces to healthcare data sources is located behind a communications gateway, an IT device that separates different networks and routes data between those networks. The communications hub might have (using IT terms) the functionality of an access point (AP), a hotspot, a router, a bridge, a switch, or a cellular-tower. As used in this embodiment, the communications gateway also has software features for formatting messages appropriate to the receiving medium as described later and facilitating a connection between the communication module, communications hub or alternative communication to other devices with the user's digital environment. In this disclosure the gateway may also support functions such as protocol validation (is the message properly formatted?), message-verification (did the message arrive from a known source, was the transmitted message received by the destination), and application-level routing (gateway receives a message indicating a message was not delivered, checks with the rules engine to determine the escalation policy, and transmits a copy of the message to the next device on the escalation list). In one embodiment, the gateway may also route the incoming message via a programming interface to partners who may choose to license the various components of the sensor-enabled packaging.

General Overview

A packaging management system in accordance with one exemplary embodiment of the present disclosure comprises the following: a configurable packaging system that has a modular communications component which can communicate with or monitor sensor-enabled compartments or sub-packages; a digital packaging manifest describing both the contents of each monitored compartment or sub-package contained within the packaging system and the rules by which each should be consumed; a system of globally unique digital and physical identifiers (e.g. globally unique identifiers [GUIDs]) to granularly identify, manage and monitor the packaging compartment's contents; a digital repository capable of creating, scheduling, routing and recording communication to the packaging user and mechanisms to analyze and visualize usage and consumption information regarding the status of the package's unique contents described in the packaging content manifest.

By combining a uniquely identifiable, disposable packaging system and a digital manifest capable of profiling the ideal usage expectations, this invention provides a new form of highly intelligent, yet disposable packaging that can track the individual usage of delivered goods once they reach to the final user.

The package's content manifest enables the content profile and usage information to be uniquely associated with each package and the individual content compartment(s) through a system of unique digital and visual compartmental identifiers. The manifest may reside as a file on a cloud-based server, within the sensor-enabled package, or on an intermediate device such as a personal computer (PC), smart phone, smart watch, television, computer or similar computing device or compatible reader pad that has the ability to connect to a network such as a wireless local area network (WLAN), or any combination thereof. These unique compartment identifiers, combined with the unique digital identifier associated with each sensor enabled communication module (as described later), can be permanently embedded during the manufacturing process or embedded later during a post-manufacturing user-provisioning process. During the manufacturing process of each sensor-enabled package, a digital manifest is concurrently created and stored, as necessary, with the unique digital identifier irrevocably associated with a corresponding digital packaging manifest.

After the package's compartments or sub-packages have been provisioned with their specific contents, the digital content manifest is completed (including the usage and notification rules associated with each compartment), and the package is affixed or sealed with the appropriate lid or cover, matching the lid to the appropriate number of individual compartments. Alternatively, a modular label containing electrically conductive traces and/or other electronic components may be applied to the package, such as described with reference to the examples of FIGS. 21-23. The package is then logged into the system as a "fully provisioned" package ready for delivery and remote usage monitoring based on the guidelines for usage, monitoring, notification, information sharing and re-ordering as outlined in the content manifest.

Because each content compartment within the corresponding packaging system is associated with the individual compartment contents described in the content manifest, the provenance, usage, consumption, and disposal of the packaging contents can be monitored, tracked and actively managed through its product distribution life cycle. Content product usage, ingredients, original manufacturer, lot number, environmental limitations such as temperature, expirations, dangerous interactions, notifications, manufacturer recalls, disposal methods, ad hoc augmentations, are all elements that can be monitored based on the content item characteristics and usage profiles outlined in the content manifest. This data may be printed on the lid itself or enclosed as a content, manifest summary.

Once delivered and activated, the package establishes a connection via a highly automated, digital communication synchronization module designed to identify and communicate with the server, typically through an industry-standard wireless connection for at least one hop and using secure network protocols. Depending on the security required, this synchronization can combine unique identifiers, passwords, certificates and the like to establish a highly secure, authenticated connection to communicate the usage events related to the activity associated with each packaging compartment. Utilizing various secure forms of encrypted digital communication, the resulting usage activity is recorded and updated in the cloud or server-based content manifest activity log.

By combining and analyzing the data and usage activity logs stored in the digital manifest repository, an authorized user can: identify significant usage trends, provide for ad hoc computability queries (e.g. prescription drug interaction queries) trigger re-orders, receive other notifications (e.g. expiration or manufacturer recall notices), receive reminders and initiate external digital processes. As an example of external processes, the system could use data collected from other digital devices (e.g. Bluetooth (BT) enabled scales, blood pressure cuffs, sleep monitoring devices, glucose monitors) and create an "anticipatory system" capable of helping initiate other reactions to the sensor input being received; one such example might involve a patient diagnosed with congestive heart failure should the patient experience rapid weight gain (indicating fluid accumulation), the system may include rules from the physician that instruct the user to take a diuretic; the system could be provisioned to provide notices to the user to assist him in following the physician's instructions.

In another example, the pharmaceutical usage data could be gathered periodically and converted into confidential drug auction submissions. This system would create an anonymous bidding system whereby pharmaceutical companies could bid for fulfilling drug regimens for individual patients. As a result, patients could be assured they are receiving the price reductions made available in a highly competitive and automated drug re-order system. In yet another example, this system addresses the known problem of patient drug interaction caused by prescription fulfillment from multiple pharmacies. As an aggregation point for prescription data, this system allows the pharmacist to compare multiple prescriptions from multiple prescribers to ensure drug interactions do not occur.

Through data aggregation, the usage and other data parameters allows for big data analysis to support retrospective and prospective analyses. These analyses serve to detect adverse or beneficial drug interactions. They enable better understanding of long-term effects of drug use and support longitudinal studies. By supporting user feedback, such as "nausea," "sleepy," "odd-taste," and/or interfacing with physiological measurement systems that provide data including: weight, blood pressure, heart rate, blood glucose levels, physiological variability, respiration rate, the collection of digital manifests/usage/feedback/physiological parameter data becomes a rich data source from which to learn. The analyses can also be used for A-B testing of different form factors, software features, and annunciations to determine which lead to the best compliance rates. Similarly, different educational segments that are transmitted to the patient's interface device as a function of compliance rate and drugs prescribed can be test. Educational segments may be requested by the patient (e.g. when a patient is curious to know more about a prescribed drug). Information may be acquired via access to web-based resources such as openFDA. Targeted ads may be provided to the user based on activity, drug regimen, compliance rates, and the like. These ads may be displayed on a smart phone, smart TV, PC, streaming media (such as Amazon Video) or on a conventional TV. Access to the de-identified data, analysis results from data studies and the like may be sold as services. The unique ID on the sensor-enabled packaging helps verify the integrity of the data used in these sorts of analysis.

Although pharmaceutical examples are used throughout this document, the smart packaging and management concepts can be used for any packaged product. Non-limiting examples include orthopedic hardware kits, documents, palletized shipments, container shipments, shipments of valuables, etc.

Packaging System Overview

As shown by FIG. 1, the system comprises a sensor-enabled package for holding medications or other contents (e.g. medical device components) in any form. As will be described in more detail hereafter, the usage activity generated by the sensor-enabled packaging consists of one or more usage events and environmental thresholds that can trigger communication from the system. The rules governing the usage of the enclosed contents are created and stored in a digital manifest that is tied to the unique identifier embedded in every provisioned sensor-enabled package. Activities and communications related to the enforcement of these rules are eventually stored as part of the manifest activity record. Data for manifests including manifest transaction activity, rules and other data associated with any specific sensor-enabled package may be held in a single repository or distributed locally. Distribution may be determined by geographic area, function (e.g. rules in one physical or logical location and contents of the sensor enabled package (SEP) in another physical or logical location), by date, by provisioning entity (e.g. if a pharmacy does all the packaging, provisioning, distribution and retail sale, that pharmacy may need to retain full control of all the data), etc.

Connecting Sensor-Enabled Packages to the Manifest Server

The sensor-enabled package may obtain a network connection via the communication hub, which in turn has a WAN connection that supports communication to the manifest repository where digital packaging manifests can be stored, referenced, and managed. The servers that comprise the manifest repository coordinate data transactions with the distributed base of sensor-enabled packages. In one exemplary embodiment, a wireless signal (such as Bluetooth, Bluetooth low energy, Bluetooth Smart, Wi-Fi (including Wi-Fi Direct), radio frequency identification (RFID), Near Field Communication (NFC), ZigBee, 802.15.4, ANT, cellular or proprietary solution) is transmitted by the communication module attached to the sensor-enabled packaging to the communications hub (e.g. base station, router, cell phone, smart watch, access-point, Wi-Fi hotspot, cellular tower), thereby gaining network access. The communication hub might have a display and or it might have communication to another device (smart TV, smart phone, table, PC, etc.) that has a display. The communication hub may have knowledge of the rules for the SEP and display messages; alternately, it may cause other devices to display messages. This is helpful in the case where the communication with the rules engine fails for some reason. In other cases, the rules engine may cause the communication hub or other display that the system determines is local to the user to display messages.

The system may be used over specific cellular networks, such as using an AT&T, Verizon, Sprint, or other cellular modem. Alternately, the system may utilize a mobile virtual network operator MVNO such as is used by some pre-paid cellular access services or such as Google Fi. In another scenario, an MVNO business is created and the system uses that cellular access and sets the data and usage rates. The system may provide incentives for customers that provide additional data or feedback on the system.

Wired links, such as serial peripheral interface (SPI), I2C, CAN bus, Ethernet, n-wire serial, universal serial bus (USB), RS-232, RS-423 and the like may be used in other embodiments to connect the communication module to the communication hub. In yet other embodiments, the communication module may itself provide network connectivity, for example, using Internet Protocol (IP) over a cellular radio.

Managing Delivery of Packages and Managing Authentication

In one exemplary embodiment, the fully-provisioned, sensor-enabled package is delivered to a user who is taking the medications contained in the SEP. The end-user may confirm delivery of the sensor-enabled package by electronically relaying the unique identifier (such as a human-readable serial number, machine-readable serial number including bar code, combination of serial number & lot number, etc.) to the manifest repository. Any one of many methods (e.g. bar code reader, digital camera, reading the identifier and manually entering it, reading the identifier from an RFID/NFC chip, reading the identifier stored in a memory via an interface to the packaging, etc.) may be used to import the SEP's unique identifier into a software application or interface that relays the data to the manifest server. Some solutions, such as NFC support a meta-message indicating what application should be used to process the data; for example, a smart-phone NFC reader may have registered the application that should be spawned when a particular meta-message in the NFC packet is received. If the meta-message indicates that the SEP application, then the SEP application is started and it processes the data including steps such as displaying the ID on the display of the smartphone and transmitting it to the manifest server. Meta messages may be included in solutions other than NFC, such as Bluetooth smart. In order to begin using the sensor-enabled package, the protective cover is removed from the sensor-enabled package and this removal activates a communication module. This activation step may trigger the system to begin event tracking, such as by elapsed time. Location tracking may be used to verify the shipped medication arrives to the proper location in a timely fashion and if not, send notifications to various people such as the patient, the caregiver, the insurer and the prescriber. Other systems, such as beacons that are part of the Apple IOS 7 release may be used to verify the user has received the SEP when the SEP's beacon is received by the user's iPhone. Other methods may be used to verify the correct user has received the package, such as biometric, personal identification number (PIN), password, and/or passphrase confirmation. For example, after the communication module is activated, other system components that support rich user interface may prompt the user for a PIN; receipt of this PIN by the user may verify receipt by the proper recipient. Other verification methods including detection of a known electronic device, such as the user's cell-phone; Wi-Fi Media Access Control (MAC) address, BT address, or cellular electronic serial number may also be used. During initial provisioning of the user's system or at a later time, the user may add new electronic devices. Adding these devices may be verified using solutions such as two-factor authentication.

In the case of a SEP that has no ability to track usage (for example, one that is designed to have a re-usable communication module attached upon receipt by the final user), when the SEP is attached to the communication module, the module identifies any compartments that have already been breached. If the user confirms he breached the compartments before attaching the communication module as may occur if the SEP arrives late, only the usage information is transmitted to the manifest repository. The user may be prompted for the date and time each was breached. If the user indicates he did not breach the compartments, notification of a failed shipment failure may be transmitted to the manifest repository. Depending on the rules configured for that SEP, the system may instruct the user to not take use any of the items, not to use the breached compartments, trigger an automatic re-order, or other response.

Other physical implementations are possible. For the sake of clarity, the descriptions in this specification assume a model where a "dumb" set of containers is sealed with a "smart" lid; however, all the features described could be implemented with a "smart" container and a "dumb" lid and the specification should be interpreted this way. In another non-limiting example, the "smart" lid might be a sensor in a pen, such as the Novalog Flexpen, which is used to dispense insulin. The smart lid detects the amount of insulin measured and injected. Imagine that the Novalog Flexpen is smart and receives notices that the user has five new vials of insulin. Each time the user injects insulin, the amount of insulin is recorded in the manifest. The system may also connect to the user's glucometer, so a correlation of insulin and blood sugar level are recorded that may be analyzed to determine improvements in the diet and/or pharmacological regimen. The pen may learn the user's typical dosing requirements and send a notification when less than 1 dose remains in the pen. For example, perhaps 1.5 cc of insulin is the current dose and only 1 cc remains. After the user injects the 1 cc and inserts the new vial of insulin, the pen automatically sets the dosage level for the remaining 0.5 cc. Further, if the user does not complete the dosage, the system transmits a notification. The pen also tracks how many vials have been inserted, emptied, and removed, which, in turn, causes the system to prompt the user to order more insulin.

Communicating with Sensor-Enabled Packages

Though the system may utilize established industry standards (e.g. electronic data interchange, Bluetooth, extended markup language (XML), TCP-IP, etc.), the invention may also rely on a proprietary electronic manifest that contains a mix of profile, usage rules, content descriptions, security information and other data parameters that guides the package's uses through its entire life cycle. The manifest may be self-descriptive using solutions (analogous to XML).

Leveraging the invention's various system components, the digital manifest will be referenced as the system updates, monitors, manages, stores and responds to the actions and activities. In various instantiations of the invention, the system will leverage bi-directional communication. The bi-directional nature of the communication does not require, and is not limited to, the originating sensor enabled package. The communication stream may originate from the package's communication module, while a corresponding, related bi-directional response maybe routed to some other device within the user's digital environment, as specified by the digital contents manifest. These responses can range from simple notifications such as "Time to take your synthroid from compartment 1" to more complex responses involving multiple system responses and notification escalations. Notifications may be local to the SEP using audio (speaker), visual (LEDs, display), or mechanical mechanisms (vibration) and/or notifications may be annunciated by other devices. For example, if the communications hub is a smart TV, the TV may turn on, place a visual indication on the screen, and produce sounds to help ensure the user detects the notification. In another embodiment, a "headless" communications hub or the communications gateway may send a notification to another device, including devices such as a smart phone, smart TV, tablet, thus enabling this other device to provide the notification. Each device may track relative locations using for example, GPS, BT smart beacons, or the like and provide notifications when the distance between these devices exceeds a limit, for example to detect the user has left the home and the medications are in the home. The system may take into account the user's calendar as part of this, for example: The system detects the user is in the car, perhaps using location or by detecting the BT radio in the car is proximal and that the SEP is not in the car. The system further checks the user's calendar and sees a flight scheduled in 2 hours. This combination of events causes the system to transmit a notification to the car's BT-enabled entertainment system, "Please check that your medications are with you." The user may tailor notification preferences to trigger on different events, separation distances, calendar agendas, etc.

A communication hub includes any receive &transmission device (e.g. smartphone) that serves as the first point of communications connectivity capable of relaying sensor event data from the SEP's communication module to the cloud-based server that hosts the manifest repository, notifications and communication server, rules engine and healthcare data source interface server. Other types of communications hubs are possible and could include desk-top computer, laptop computer, tablet computer, personal digital assistant (PDA), wireless router, local area network, smartwatch, smart TV or other next generation wireless and digital communication devices that are within the transmission range of the sensor-enabled packaging's communication module. As stated earlier the SEP package's communication module could also act its own communication hub if it is equipped with the necessary technology to facilitate its own direct communication to the cloud-based server (e.g. cellular-based communication module). The communication hub may have high power, a very low receiver sensitivity and/or high-gain antennas to support communication with sensors at long range. The communication hub might support multiple radio technologies, such as the Qualcomm 2net product. The communication hub might be shared with other applications, such as Life Alert or home fire/intruder alarm systems such as Simplisafe. The communication hub may use other features of the home to augment communication. For example, a communication hub that is ac-powered could modulate a signal onto the AC wiring in the house and that signal is detected by other devices throughout the house. Similarly, the communication module could have a mechanical connection to an ac-powered interface that augments the communication module in some way, for example: to provide power; a larger, more efficient antenna; access the AC line to transmit and receive signals throughout the home, a display and the like. The larger, more efficient antenna may improve BT, 802.11, cellular, NFC, or other transmission solutions. Any display in the system that provides user interface may include status such as number of items of each type remaining; tracking information about incoming packages, such as "prescription for Plavix has been filled and is awaiting shipment," and other information important to the use of the product.

Utilizing the Sensor-Enabled Package's Unique Identifiers

During the manufacturing process of the sensor-enabled package, each lid used to seal a sensor-enabled package may be assigned one or more unique identifiers, thus becoming part of the sensor-enabled packaging. This could be accomplished by embedding, imprinting or otherwise associating the identifiers in a chip, obscuring the identifiers in an image as is done by Digimark, or other mechanism, such as bar-code or human readable format as part of the sensor-enabled packaging. Preferably each identifier is a globally unique ID (GUID). The first identifier may be non-secure and externally readable, allowing users to confirm the identity of the package. The first identifier may be a public encryption key as is used in an asymmetric encryption scheme. For example, the private decryption key may only be known by the manifest repository server and therefore only messages received by the manifest repository server can be decrypted.

Regardless of method, the goal of this security schema is to enable the eventual user/"provisioner" to establish an indelible bond between the user's identity, the rule set established in the manifest, and the association to a specific sensor-enabled package. Whether the provisioner is an individual provisioning a single drug regimen for a relative or a pharmacy/hospital system automatically provisioning the SEP, the resulting manifest will be permanently associated with the unique identifier(s) that was (were) assigned during manufacturing to this sensor-enabled package. In the case of a hospital, the manifest may be populated using profile data from the electronic medical system (EMR) such as a drug regimen for a patient who is being discharged following a specific surgical procedure. In parallel, the order for the drugs is made and an SEP is assembled to match the content in the manifest. At this time, a public-private key pair may be generated by the manifest repository server; the public key is then transmitted to the pharmacy that is assembling the SEP. The public key may be included on the shipping label, for example.

To provide other useful data points, the communication modules (whether Bluetooth, Wi-Fi, or cellular) may also be equipped with a unique identifier. This allows the usage and event data being streamed to the cloud to include the identifiers of both the package and the communication module to be used to authenticate and, if appropriate, identify usage patterns. These communication module unique identifiers can be implemented as both internal hardware enhancements and or externally readable identifiers.

Identifying Sensor-Enabled Packages

Figure 2:
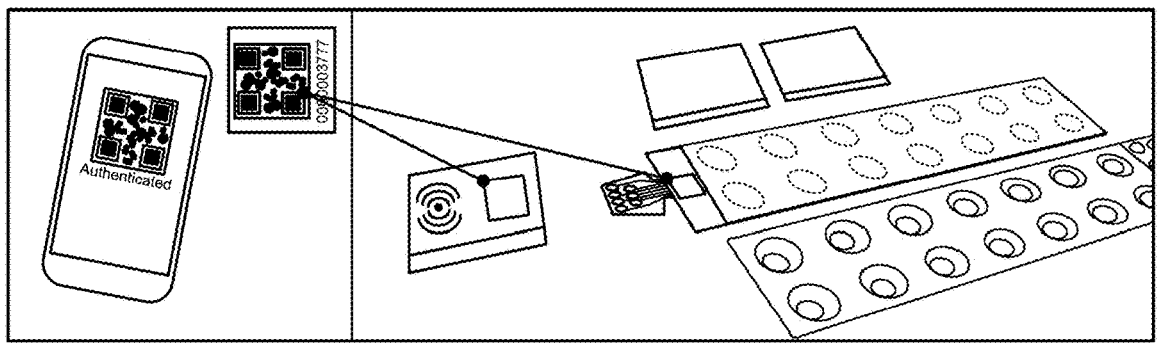
FIG. 2 depicts using a smart phone to image a bar-coded GUID to register the package and or communication module identities as part of the SEP provisioning process. This could be accomplished wirelessly—RFID/NFC.

In one embodiment, a user provisions a new SEP by launching a software application that prompts the user to identify the package. Utilizing some combination of the unique identifiers associated with every specific sensor enabled package, the user can contact the server repository to register a specific digitally enabled package to new manifest. At this point, the only content in the manifest may be the user name and the encryption keys. In one embodiment of the invention, the user may utilize a smart phone equipped with a digital camera. Using this method, as shown in FIG. 2, the application would capture (e.g. with phone's camera) images of the bar-coded GUID, using the smart phone's camera to generate a request to the manifest server.

Including the smart-phone's IMEI (aka electronic serial number) with the message is a way to verify the proper person received the SEP. This request would initiate the digital manifest provisioning process described later in the document.

In other cases, users will want to securely access an existing digital manifest via the unique identifiers associated with a specific sensor-enabled package. This invention envisions the capability of choosing either a cloud-based manifest repository or a manifest stored locally within the digital package's communication module. One use case that would benefit from the storage content manifests resident on the sensor enabled package involves Schedule II drugs; for example, with pain medications like oxycodone, the manufacturer wants to ensure various usage rules and manufacturer's warnings are always resident within the distributed package, even if there is no connection to the manifest server.

If there is a local copy of the manifest, an application on the phone could read the contents—via RFID, BT, NFC, Wi-Fi direct, Wi-Fi, BT smart, Blue Tooth low energy (BTLE), ANT, ZigBee or other method, including a wired connection—and by comparing the local copy of the manifest to the copy from the server, the application can provide an automatic content verification. Unrelated to the first external identifier, a, secret digital identifier may exist. This second GUID could be embedded into a chip such as the FLASH or EEPROM module within a microcontroller. Configuring the microcontroller to not allow external reading/dumping of the memory is a method to keep the second identifier secret. Alternately, the second key may be encrypted using public-key cryptography and then provided in human and/or machine-readable formats or stored using other mechanisms, such as in a digital memory. Another method of attaching a unique, secure key to a package is through use of a cryptographic coprocessor such as the Atmel ATECC508A that integrates ECDH (Elliptic Curve Diffie-Hellman) security protocol. The ATECC508A provides an ultra-secure hardware-based cryptographic key storage and cryptographic countermeasures that are more secure than software-based key storage.

The second GUID might be a device-specific certificate such as those used in the EAP (extensible authentication protocol) options including, but not limited to EAP-TLS, EAP-PEAP, EAP-FAST, EAP-TTLS, upon provisioning of a new packaging lid, both identifiers may be stored on the remote server within a unique blank digital packaging manifest. After the lid is affixed to a packaging body, changes to the manifest (to reflect contents of the packaging body, for example) on the server may require transmission of the encrypted data ensuring that the changes are made to the manifest that matches the provisioned packaging lid. The provisioning and update processes may require confirmation at each step that any copy of the manifest stored in the lid matches the manifest on the server. The manifest may be stored in other components of the SEP beside the lid.

This manufacturing strategy and identifier approach ensures each sensor-enabled packaging lid, once affixed to a packaging body, will create a unique package irrevocably tied to its digital manifest, thus allowing the corresponding manifest to act as the focal point for securely storing each compartment's content information, patient demographic data, contact profiles, access rules/privileges/log, security codes, usage instructions, notification schedules, usage log, etc.

Digital versions of GUIDs, including certificates, can be individually revoked and updated as needed. Security can also be enhanced by implementing a separate layer of biometric identification to, either control access to digital manifests and other security provisions, or to confirm the identity of a user as a requirement of the content usage validation. In one embodiment the rule sets within the manifest could be constructed to force users to validate their identity with the biometric capabilities within in an embedded biometric technology within the communication module (e.g. through touch screen on face of communication module) or a biometric feature resident within a separate technology platform (e.g. apple's new iPhone fingerprint reader). Other biometric methods could include but are not limited to: retinal, voice, biologic or facial recognition.

The two-identifier system allows the distributing party to use a combination of the external code (in the clear) and the embedded code (secret) to establish a secure methodology of authenticating which unique package is attempting to establish a link with the manifest repository or other system server. Based on user preference, variable levels of system security can be implemented. In one embodiment, the security algorithm could combine the embedded unique digital identifier with password protection, hardware identifiers, biometric identification or other measures to ensure the data stream is originating from an authenticated user or caregiver.

In another embodiment, a user may want to maintain complete confidentiality regarding the package's contents, but still want the benefit of the automatic medication usage guidance. In this case, the unencrypted GUID is still used to verify the user-package relationship. The application on the user's phone might specify the contents of the digital manifest for the user only and never upload the contents of the manifest. In this use case scenario, the digital record associated with a specific manifest would only include the activity events associated with the specific compartments of the sensor-enabled package without ever exposing the actual contents. The user might provide data to the server in an encrypted format using the user's own encryption key (where the decryption key is unknown to the server). This allows any of the user's devices that know the decryption key to use and update the manifest and rules with the manifest still stored on the system cloud server and therefore accessible anywhere by the user's various devices.

In another embodiment, a hash of the encrypted key and the non-encrypted key could be used as a further step to ensure a person has physical access to the SEP.

As shown in FIG. 1, the manifest repository is coupled to a communication network. This network typically comprises at least one wide area network (WAN) communication system, such as the Internet. However, the network communication system may comprise other types of networks in addition to or in lieu of the Internet. For example, the system may comprise the public switched telephone network (PSTN) and/or a cellular telephone network. The data could travel, for example, over a private network such as the DataTAC network used by Blackberry or Motorola's Integrated Digital Enhanced Network (iDEN). As shown in the sequence diagram illustrated in FIG. 3, bi-directional communication occurs between each part of the system. Acknowledgements and other communications protocol messages may also be transmitted.

Located in the cloud is a remote server, a rules engine, manifest database repository and an information gateway. Packaging usage data is received from the SEP, via the communication module, which transmits the data to the remote server via the communication hub. The usage data is compared to the expected usage schedule or events embedded within the digital packaging manifest, which was created when the sensor-enabled packaging was originally provisioned. The digital manifest records the incoming usage data, and based on such comparisons, trigger the appropriate communication to the correct recipient (e.g. patient, caregiver, relative, or administrator) and digital delivery device (e.g. cell phone, television, tablet). The remote digital manifest repository can also trigger communication independent of usage data being forwarded from the sensor-enabled packaging, based on pre-programmed events and thresholds outlined in the digital manifest.

Once an activity or usage event (e.g. package activation or compartment accessed/breached) has been received, the manifest repository uses the rules set described and recorded in that SEP's digital manifest to respond based on the stored parameters. These responses could include, but are not limited to the escalation logic needed to prepare the necessary notifications, manufacturer's warnings, messages, etc. to be transmitted back to the user's various electronic devices, including the packaging itself, through the communication hub. The nature, content, structure and format of these communications can also be impacted by the accumulated activity logs, updated rules, human intervention and the data streams from other input sources and hardware. The activity logs will also store various failure states to identify and troubleshoot system problems.

As a non-limiting example of how the interaction between the manifest, the rules engine and escalation logic could be play out, the user uses the camera to image the non-secure GUID, fills the package and attaches the sensor enabled packaging lid. The user might also image the drug and/or the pharmacy bottle to provide information to the system (such as confirming the drug being inserted is what the user thinks it is, to provide information to the system to guide the user as to dangerous drug interactions, about when to take the next dose, etc.). The user and/or the rules engine (using data from the prescription label) creates the rules regarding when notifications should be given, (e.g. 8 hours after the prior dose) and the application never has need to connect to the manifest server).

The rules engine, whether running as part of the application or on the manifest server, can include rules for what to do in the event a dosage is missed (e.g. double up on the next dosage at the normal time, take the next dose as soon as possible and continue w/original schedule, ignore the missed dose). The rules engine can also automatically generate suggested adjustments to the medication schedule and send to the appropriate caregiver for final approval. All such instructions are entered manually by the user or the user's representative (e.g. caregiver, physician, pharmacist). For example, if a medication is to be taken every 8 hours and one dose is taken 2 hours late, the notifications for the next dosage can be modified to be 8 hours from the time the medication was actually taken. Alternately, the rules engine can slowly recover from a late dose, for example by taking each of the next doses 7 hours after the prior dose. The rules engine can include interactions that may require spacing between dosages or activities. For example, Synthroid should be taken at least 30 minutes prior to eating or at least 120 minutes after eating. An anemic patient who also has a hypothyroid condition typically takes both an iron supplement and the Synthroid daily; the Synthroid and iron supplement, however, need to be space at least 4 hours apart. The rule governing the order of events prompts the user to take Synthroid, eat breakfast, and then take an iron supplement. Acting on information from the sensor-enabled packaging that indicated Synthroid was taken at 0630, the rules engine directs the user with a reminder at 0700 that it is OK to eat breakfast; and then at 11:00, the user is prompted to take the iron supplement.

In a non-limiting example, the sensor-enabled packaging may be used to monitor the medication adherence and health condition of a patient recovering from cardiac surgery. In this case, the rule set stored in the digital manifest may also require the collection of weight related patient data from a remote weight scale. The rule set, in addition to recording the adherence to a medication regimen, may also be recording the patient's weight to use an as an ancillary data trigger. In this instance when a threshold for weight gain is breached, a medical professional is notified to potentially instruct the patient to take a diuretic pill that was pre-packaged along with other pills in the patient's regimen to accommodate this contingency (see FIG. 3). If approved by the physician, communication would be sent to the patient to caregiver. The system would then add this expectation to the package's rule set as an activity event to be monitored and confirmed.

The communication gateway coordinates the delivery of the each returned communication element, formats the element for the delivery medium (e.g. text message, voice message, television screen in screen, etc.), monitors for responses or acknowledgements from the eventual recipient, partner or hardware device. All bidirectional communication events that are received or sent are recorded and logged in the appropriate digital manifest, or logged in a separate file that is logically tied to the digital manifest.

In one exemplary embodiment, the rule set attached to the digital manifest specifies that medication reminders be sent out fifteen minutes in advance of a scheduled dosage, via a cellular voice reminder or text message, directly or through the network communication system to a device (e.g. cell phone, computer, tablet, television identified in the digital manifest), which then displays the text message. If the expected sensor alert is not detected, the system executes the next rule and communication task proscribed in the escalation chart directive. In other embodiments, other types of messages or indications may be provided by the system.

Sensor-Enabled Packaging Components

Below, two exemplary embodiments of a sensor-enabled packaging are described. One consists of an array of sensors embedded in a packaging lid while other uses wireless sensors attached to the same lid structure. Each utilizes a system that consists of a unique packaging identifier, a packaging communication module docking base (PCMDB), and a data processing/communication module.

Figure 5:
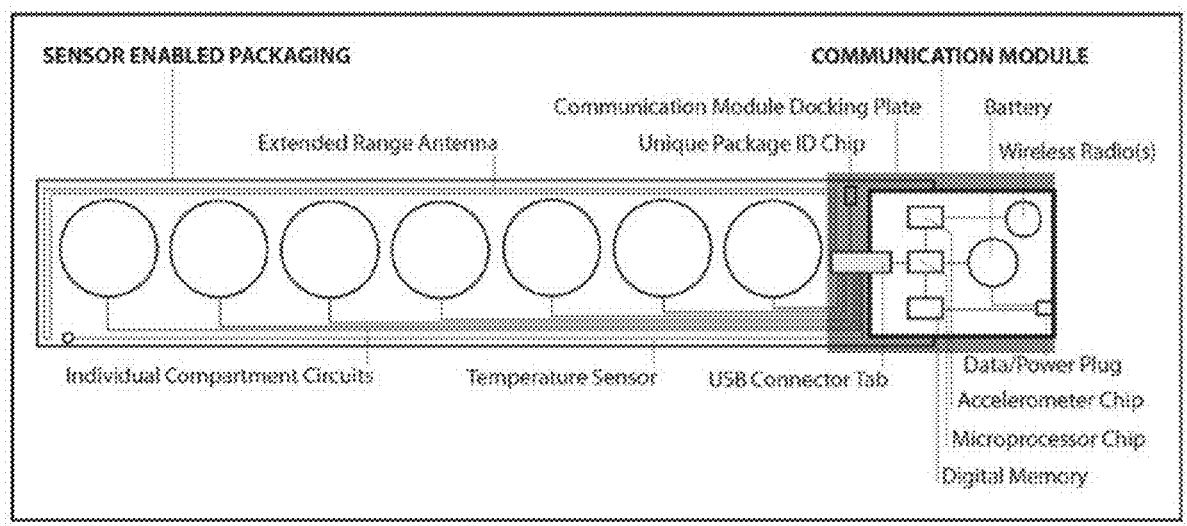
FIG. 5 depicts a seven compartment, circuit-based sensor-enabled package with a communication module.

FIG. 5 illustrates a circuit-based embodiment with an array of compartment sensors that are affixed to a lid or cover with a pre-designated set of compartment openings. These sensors are linked to a sensor-enabled lid (manufactured with sensor-enabled openings), which is attached to the matching packaging receptacles consisting of compartments of known dimensions (e.g. a tray of extruded plastic wells) once the package has been provisioned. After being provisioned with contents, the sensor-enabled lid is adhered with pre-applied adhesive or other mechanism, to the container body.

Once provisioned with contents (e.g. specific medications) and sealed with the sensor-enabled lid, the distribution authority (whoever is taking responsibility for managing the package's contents and distribution), may register the package electronically by using the external identifier to launch a software application. The software application includes an interface to populate the unique digital manifest that was created and stored for future use when the lid was manufactured. As discussed later, the distribution authority will use a software program or interface to complete the packaging process by completing the digital manifest to include the recipient's profile, contents of each compartment, reminder and escalation rules, trusted contacts and digital modes of communication, trusted third-parties, privacy provisions, etc. Once the sensor-enabled lid is permanently sealed onto the package, and the digital manifest is completed, the sensor-enabled package is considered provisioned.

Figure 4:
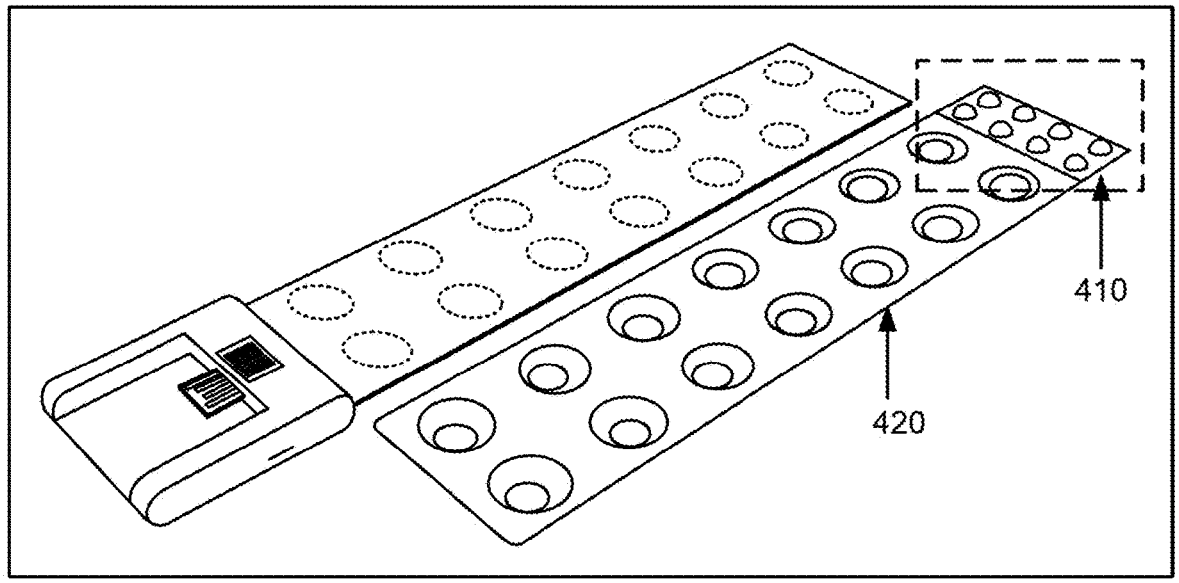
FIG. 4 depicts packaging that includes ancillary, pre-packaged medications (pills outlined at the end of the lid) to be taken under variable circumstances.

In still another embodiment, a sensor-enabled package could utilize an array of wireless sensors (illustrated in FIG. 6) rather than a circuit-based lid shown in FIGS. 4 and 5. In this example, wireless sensors are attached to separately packaged (disconnected from each other) sub-packages/compartments. Instead of sensors bonded to the openings of a package's lid to be placed on pre-configured packaging trays/compartments, wireless sensors would be separately attached to individual sub-packages which would then be wirelessly linked to the unique packaging identifier embedded in the PCMDB, which would serve to identify the overall package's identity. Once the primary packaging is opened, the PCMDB, together with its attached communication module, monitor for signals from the array of wireless sensors to determine and monitor the status of each sub-compartment. Similar to the previous embodiment, the usage rules stored in the digital manifest would be applied as the wireless usage events are detected and forwarded to the server through the communication module to the manifest repository.

FIG. 4 further depicts at 410 compartments that contain ancillary contents, such as ancillary medications, diagnostics (e.g., test strips), and/or devices (e.g., injectors, etc.) to be used in conjunction with medications contained in compartments depicted at 420. As an example, Narcan™ (e.g., within a nose spray dispenser for the treatment of opioid overdose) may be provided as an ancillary contents in a compartment at 410 for an opioid-based medication provided in a compartment at 420. Accordingly, as described in further detail herein, the monitoring of compartment states (e.g., open or closed) via electrically conductive pathways may support different functions, including determining the compartment state of a compartment (e.g., 420) containing an opioid-based medication and determining the compartment state of a compartment (e.g., 410) containing ancillary contents.

The packaging may be designed to support multiple form factors, including for example, a communication module being located at the center of a circularly-arranged blister pack, such as the type commonly used for hormone therapy (e.g. the 28-day blister pack used for birth control pills). In this example, an interface region containing pins or other terminating ends of electrically conductive circuits may having a circular or semi-circular (e.g., arc-shaped) configuration on an interior edge of the packaging to interface with the communication module. It may be built into the cap of a medical ointment to verify the usage of the ointment and may have a method to determine the amount of ointment used. Each day/week/time-of-day may have a different marking to provide indications of when the particular drug would be taken. Research studies show that different form factors lead to different compliance rates. Any packaging solution that has ability to detect when a medication was accessed is within the scope and spirit of the invention.

Sensor-Enabled Packages and Related Components

Figure 6:
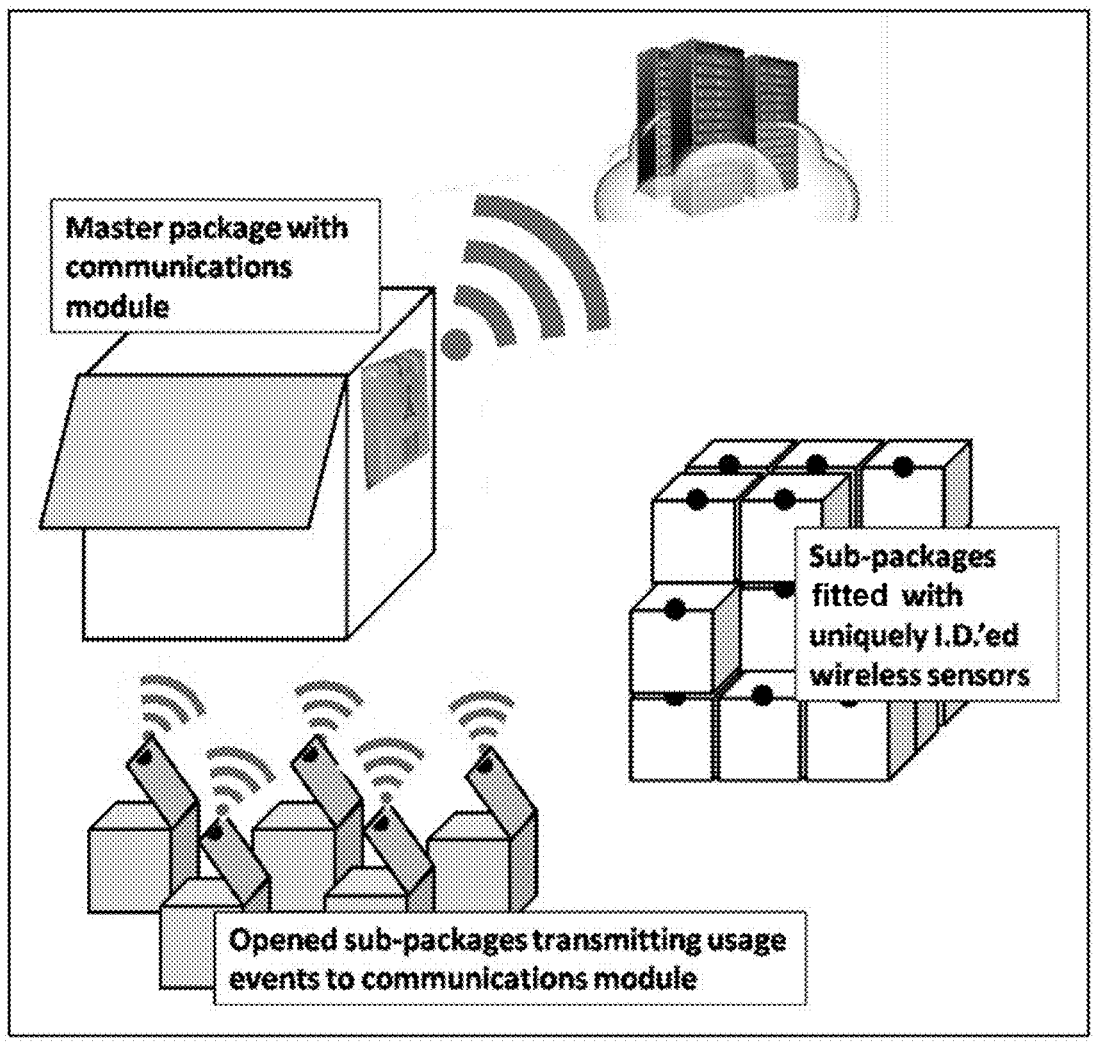
FIG. 6 depicts sensor-enabled packaging utilizing wireless sensors to monitor the various sub-packages contained in the original packaging in which the illustration shows that five sub-packages have been opened and are separately signaling the communication module mounted on the original package.

As shown in FIG. 6, the sensor-enabled packaging relies on a set of compartment sensor(s) that monitor the status of specific package compartments or sub-packages. The individual compartment sensors can be connected to the processor module via a variety of techniques, which could include, but are not limited to, physical electrical circuits linking each individual packaging compartment to the processor module and communication module. In one embodiment, the circuits in the lid would also link a pre-printed circuitry lining adhered to the lower part of the package's individual compartments. By linking the circuitry in the compartments to the circuitry in the sensor-enabled lid, the communication module would be able to monitor the entire sealed compartment and thus deliver even more rigorous content security. Another method of monitoring could include using individual wireless sensors capable of sending a signal when triggered to the processing module using a wireless signal. In this embodiment the wireless sensors would be capable of harvesting energy from the environment or human touch to perform their sensing function. As an example, a radioactive source with a short half-life could be used for the energy source and also to provide timing. If the particles are alpha particles, they wouldn't pass through the plastic and if the half-life is short, then timing to an accuracy of tens of minutes could be achieved by detecting the rate of emitted particles.

The lid, or associated sensor enabled packaging, may have several different methods of communication and storage, depending on the use case. In one embodiment, a simple lid monitors physical circuits that allow the communication module, when inserted into the PCMDB, to detect all aspects of opening events and identify the PCMDB's unique digital identifier. That is the lid only provides an electrical contact that allows the external device to sense if/when a compartment is opened. External devices (e.g. digital scale, blood pressure cuffs, etc.), including and working in tandem with the communication module, could provide additional processing and/or functions, which might include providing power, date/time, manifest read/write/storage, event recording (including environmental conditions), rules engine updates, and implementation of rules.

Advanced Rules Management

Prospective rules engine updates to the digital manifest could include changes triggered by new parameters inputted through the rules engine, including in a non-limiting example, updates to the rules that account for user's behavior and actual use of the medication (i.e., the rules engine indicates to take the medication at 0600, but it is always taken at 0700; as a result, updates based on prescription changes, formulary changes, based on activity, e.g. having eaten or having taken another medication that has an interaction with another medication stored in another compartment.) Implementation of rules includes processing and executing the requirements of the rules engine (e.g. providing an alert on the user's smart phone when a medication is to be taken and escalating the alert to a caregiver's smart phone if no activity is detected).

In another embodiment, the lid might utilize a more complex communication module having all the functionality required to track all events, provide rechargeable power, store and forward data, date/time stamp, store/update/transmit and read the local manifest, read/update an external manifest, rules engine updates, implementation of rules, and manage interaction with other devices being managed as part of the overall manifest rule set.

An application, such as might run on a smart phone, tablet, smart watch PDA, pager, set-top box, smart TV, automobile computer, tablet, PC, or other computing device could be deployed within the communication module to manage the communication with other device and applications. In this case, the lid may contain a power source, radio, microprocessor, clock, and/or various event detectors to determine when events occur. These connections from the event detector to the CPU (or other device that logs the event) may be wired or wireless. Similarly, connections from a CPU on the lid to an external device could be wired or wireless. Wired solutions include, but are not limited to, USB, I2C, SPI, UART, USART, parallel, SATA, n-wire serial, Ethernet, etc. Wireless solutions include, but are not limited to, RFID, NFC, ANT, BT, BTLE, Wi-Fi, cellular, 802.15.4, or other standards-based radio or a proprietary radio to communicate wirelessly either to another component on the system or to an external device.

Both the extent to which events trigger logging and the complexity of the system can vary with the use case and the capabilities of the deployed SEP. For example the lid might only log the event along with its date and time and await reading by and external device via wired connection or when a communication module is attached. A microcontroller with a real-time clock, ability to detect events via digital input state changes and ability to program an NFC chip is an example hardware solution that supports this concept. In contrast, a higher-functionality SEP might have more power, memory, and a communication means so that it can immediately transmit to the communications hub events instead of waiting for a communication module to be attached. Regarding logging events, it could be that the act of triggering an opening event itself provides power enough to the system to allow it to log the event. For example, the mechanical motion of removing the cover from a compartment could, through release of either mechanical or electrical energy, provide the power to signal the communication module of a compartment opening. The energy might be stored (potential energy) and released upon opening or kinetic energy, due to the motion of removing the cover. For example, removing the cover could allow the detection of light, which is turned into electrical energy via a solar cell. If opening the compartment lid causes frictional motion between two materials, a static charge and resulting detectable voltage difference may result due to the triboelectric effect.

Power Sources

Power sources to support the detection of usage events, event storage/processing and communication could include, but are not limited to: external DC power (including standard solutions such as USB and eSATA), rechargeable battery including Li++, Alkaline, button cell, paper battery, printable battery, and energy mining (mechanical, thermal, RF, solar or any combination thereof), nuclear, and the triboelectric effect. Using short half-life isotopes that release alpha particles, energy could be generated and time stamped, since provisioning could be identified based the decay of the radioactive material. Paper batteries allow for a form factor that may be used, and printable batteries could be laid down as part of the printed circuit board. Zinc Air batteries may be used and have a feature that they don't discharge until there is contact with Oxygen, as when the protective cover for the lid is removed. Power sources may be configured to allow short-term, limited functionality prior to removal of the protective cover but otherwise the power source is not used. As an example, if a particular input is set, the central processing unit (CPU) might allow provisioning of manifest data and then shut-down or go into another low-power state until detection of an event such as opening a compartment or removal of the protective cover is detected. Removal of the cover might automatically pull a resistive layer that inhibits battery contact until it has been removed. A system with a rechargeable battery might support charging via DC power source (such as USB or AC-DC adapter), wireless charging, for example that supported by the Qi standard, or through energy harvesting. The system may support both external power and internal power sources, including near-field/NFC energy harvesting.

In addition to the packaging sensors, the sensor-enabled packaging lids are also comprised of set of basic functional processing and support components. These could include a power source, unique digital identifier module, processor module, wireless communication module and simple status lights. The exact configuration of these modules, however, could differ depending on the lids design and intended use.

Electronic Components of the Sensor-Enabled Lid

In one embodiment of the invention, the sensor-enabled lid could be equipped with a set of embedded or modular electronic components designed to support a variety of use case models. In another embodiment the sensor-enabled package would be permanently fused with all the functional components which could include, but are not limited to: an unique digital identifier, processing unit which would have the capability to store and report sensor and internal processor feedback, the internal status of other hardware components; and any connected processing and communication modules. The processor unit would record the data parameters associated with any specific sensor event (time of day, elapsed time, environmental conditions, and any other data the sensor or the processor can quantify, monitor or measure). These parameters would be available for immediate transmission back to the cloud or could be stored for later electronic delivery. These data parameters would be combined with the unique identifier for both the individual packaging compartment associated with the sensor event and/or the unique sensor-enabled packaging lid identifier to ensure each sensor event data transaction can be associated with its unique digital packaging manifest after being securely transmitted to the remote server and (or) a detachable, re-usable communication module.

Modular Processing/Communication Module

In one embodiment of the sensor-enabled packaging, a complete lid is comprised of various components (e.g. power source, processor module and wireless communication module) that are combined into a separate processing and communication module. In this embodiment, the communication module can be integrated as a separate, detachable module and enhanced with additional capabilities (e.g. accelerometer, rechargeable battery, unique device identifier, support for physical cable attachment, etc.) to allow the detachable processing and communication module to be re-used on compatible packaging. The detachable processing and communication module illustrated in FIG. 6. would be attached—by way of a connector, clip or other methods suitable to securely connect the detachable processing and communication module—to the sensor-enabled packaging and sensors. A USB connector is one example that supports power and data transmission. A user could also simulate a communication module with use of a special cable, so it can be directly connected to a communications hub. The detachable communication module may support cellular, Bluetooth, Wi-Fi, or other communication protocol and may support multiple communication protocols.

Communication Module Also Acting as a Communication Hub

Figure 7:
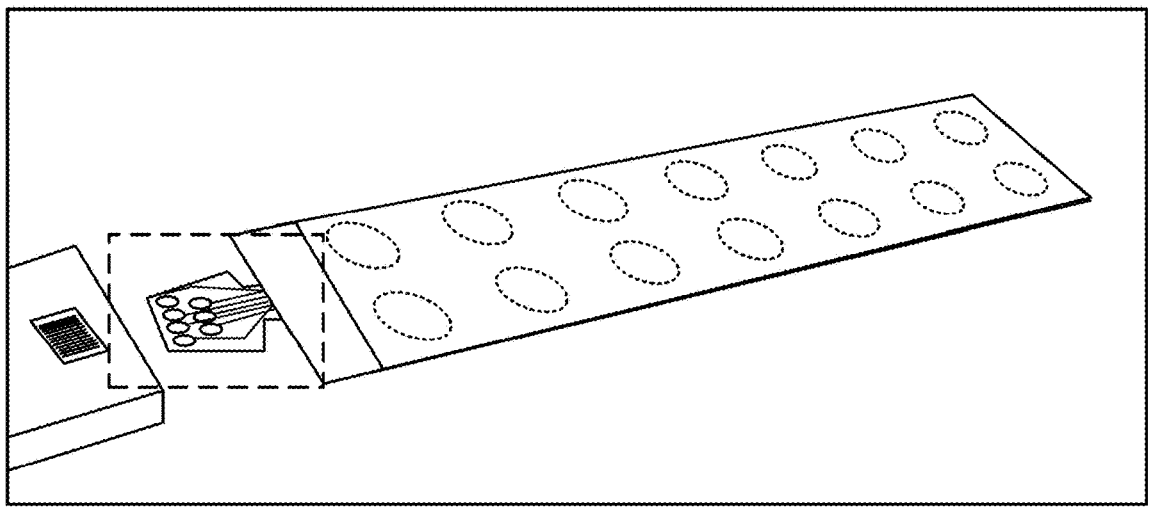
FIG. 7 depicts a packaging lid "connection tab" (on the left) being inserted into a communication module.

In another embodiment, as shown in FIG. 7, a detachable communication module could be designed to not only provide its own processing capabilities and wireless communication connectivity to a separate communications hub, but it could also act as its own communication hub and therefore coordinate the communication connectivity for other, less technically sophisticated communication modules (e.g. Bluetooth scales, blood pressure cuff, sleep monitoring devices). One example of how this technical scenario might be implemented would be for a cellular- and Bluetooth-enabled communication module to act as a communication hub for other Bluetooth-enabled packages. In this scenario, the SEP's communication module would serve as the "master" in the personal area network, connect with the Bluetooth communication modules and relay their status, activity events, and other data through the master communication module's connectivity. Being without a display, the user interface for the communication module may be expanded through using the display of another device, such as a tablet, to configure the communication module, such as pairing to other Bluetooth devices.

This combination of subordinate and master communication modules represents a novel solution to the situation of supporting temporary/ancillary drug consumption while a patient simultaneously maintains a consistent drug regime. In this embodiment, a patient could be equipped withal cellular-based communication module for their usage with chronic drug regime, but as addition episodic medication or treatments were added, these could be deployed using less expensive/sophisticated Bluetooth support modules.

To streamline support activities between a cellular communication module (master communication module) and Bluetooth communication modules (such as seamless pairing, hardware status checking, signal; quality, etc.), a user could remotely access the cellular communication module from a screen-equipped device (personal computer, tablet, Smartphone). After being validated from a security perspective, the remote administrator could utilize the local processing, connectivity tools and software resident on the cellular-based master communication module to manage the temporary/transient network of authorized Bluetooth or wireless devices (weight scales, blood pressure, sleep monitoring and other sensor-enabled devices). In another embodiment the communication module could be equipped with a touch screen to enable more sophisticated, localized support and direct user feedback.

Figure 8:
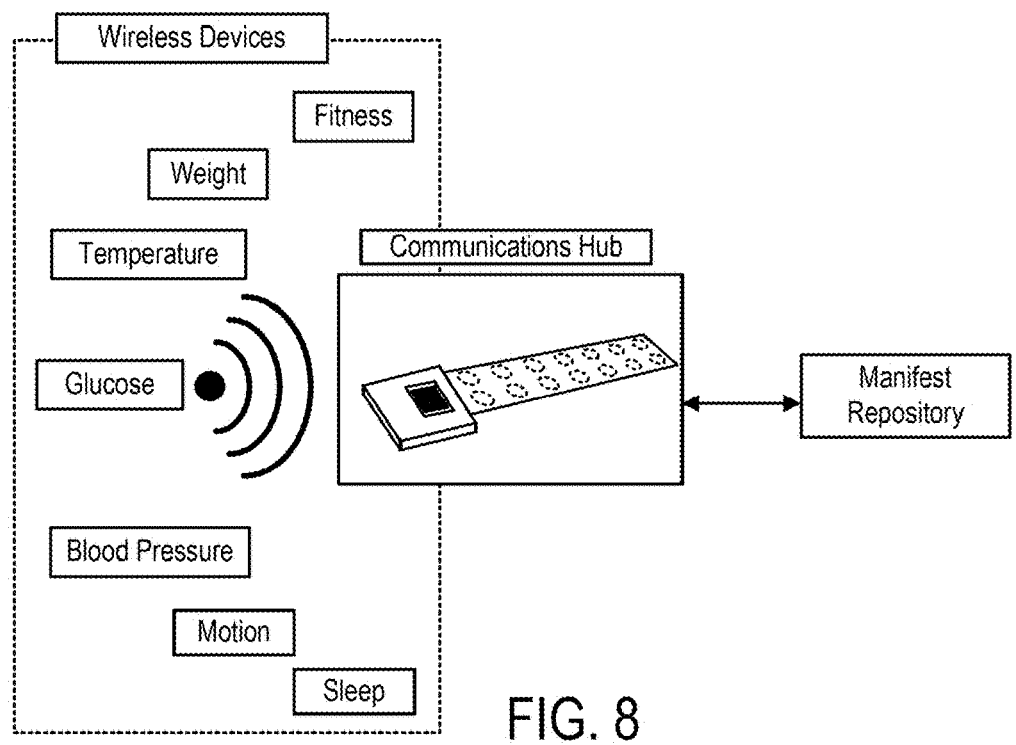
FIG. 8 depicts wireless devices interacting with a cellular-base communication module attached to a sensor-enabled package acting as a communications hub.
Figure 9:
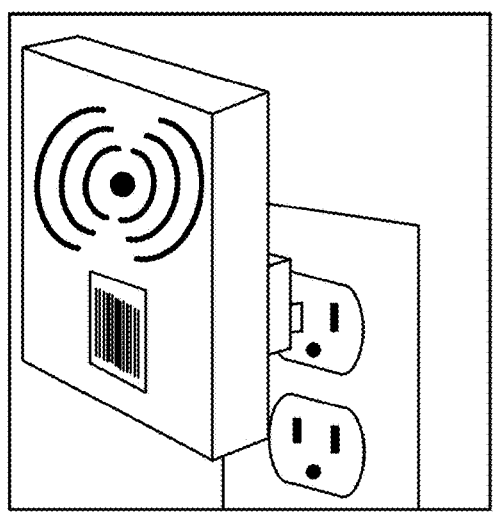
FIG. 9 depicts a communication module docked to a modular connector that can allow it to be mounted into an electrical outlet.

In one embodiment of the invention, we leverage the modular design of the communication module to allow it to be utilized as a stand-alone communication module/wireless hub (FIG. 8). In this configuration the communication module is attached to a docking station that can be plugged to the wall directly or with the use of power cord. In addition to leveraging a continuous power source, this embodiment could allow for extended signal range and an advanced feature set allowing it to better coordinate the communications of other devices, including, but not limited to, other packaging and Bluetooth devices described elsewhere in the document.

Sensor-Enabled Packaging Lid Coverings

The sensor-enabled packaging lid is manufactured with integrated sensors, which are designed to detect when the package is activated for use or when the packaging compartment openings are peeled, punctured or opened in any way. Once attached to the package body, the sensors integrated into the sensor-enabled lid detect when a packaging compartment(s) has been opened, thus and triggering either a passive or active signal to the processor chip and other electronics within the communication module to relay a signal to the communication hub and reporting the usage event. If the communication hub is not available, a store-and-forward communication model may be used, in which the communication module saves the event data until such time a connection to the communication hub is available and data can be forwarded to the cloud-based manifest repository.

The SEP might support direct IP connectivity, so updates can be sent directly to an external device anywhere on the Internet. As an example, if the SEP supports a cellular radio, Wi-Fi radio or BT smart, the Bluetooth module itself may support an IP connection, including IPV6. Alternately, an SEP supporting a non-IP protocol that connects to a bridge, such as a cellular telephone may receive software updates that are received by the cellular telephone and delivered to the SEP over a non-IP protocol such as BT Classic or USB. Software updates may use authentication and encryption to ensure that the supplied software is authentic. The software could be uploaded over a non-IP wired connection of type mentioned elsewhere in the disclosure or over a non-IP wireless connection of type mentioned elsewhere in the disclosure. As a specific and non-limiting example, an application on a smartphone could make a connection to the CPU over a BTLE link and update the software on the lid's CPU. The application could allow the user to actively manage this activity or be passive and just provide the connection to a server in the cloud that provides the software update. Software updates could add additional functionality, change licensing structure, improve performance or provide bug fixes.

Regardless of whether the processing and communication module is embedded or detachable, the sensor-enabled packaging lid may rely on a separate sensor to detect the activation or opening of the provisioned sensor-enabled packaging compartment or compartments. Whether triggered upon the removal of the protective cover from the sensor-enabled packaging lid or a user-trigger signal is generated, this activation notification signals the communication module to forward an activation notification and unique digital packaging identifier, through the communication pathway described earlier, to the remote server hosting the corresponding digital manifests. Like all usage events, this activation event is recorded in corresponding digital manifest whether the manifest is stored locally on communication module or in the cloud-based manifest server. Even if no activation notification is sent, notifications signaling compartments are being opened would be used as a default indication a package has been activated by the end user.

Non-limiting examples of various methods for detection of a breached compartment follow. In one embodiment, the CPU has an internal resistor that either pulls the signal level on a general-purpose input-output (GPIO) pin up to a logic-high voltage or down to a logic-low voltage. Assuming the case of a logic-high pull-up, then when the compartment has not been breached, the lid provides for a connection from the GPIO to ground. When the compartment is breached, the connection to ground is broken and the weak pull-up to logic high internal to the CPU results in a logic-level change that is detected. The pull up/pull-down resistor may be external to the CPU. Other logic such as a state machine implemented with logic gates as with an FPGA may be used. A simple solution might only link the event of breaching the cover and the state of the latch being read by an external device. In this solution, the exact date and time may not be known, and date/time precision depends on how soon after breaching the compartment an external device reads the state. If each compartment has a different valued pull-up/pull-down resistor and the connections are combined in a wired-OR function, then for proper resistor values, digitizing the voltage on a single input to an A/D (possibly within the microcontroller) provides information on all the compartments that have been opened because the sum of the voltages for any set of opened compartments is unique. The wired-OR function can also be used to trigger an interrupt when any one of the compartments is opened. Other resistive solutions exist; for example placing many such resistors together provides functionality similar to a restive touch screen where the position is detected by knowing the resistive change in both the x and y axes. Distributed resistance may be used as with a touch screen. A resistive touch screen solution may also be used so that a grid covers the surface and the touch screen controller detects which compartment was touched/breached. Each compartment might feed a unique interrupt input. Capacitive changes may be used to detect a compartment opening, for example using Microchip Technology CAP1114 or using a capacitive touch-screen-like solution that has similar location detection features as the resistive touch screen. An event such as opening a compartment might feed an interrupt on a CPU, causing the CPU to move from a low-power state to log the event including for example, the compartment number, date, time, GUID(s), update the rules engine, revoke/suspend any existing notifications. Notifications may include, but are not limited to: medications out of date, drug interactions, time to take a medication, past-time to take medication, alterations in the medication due to non-compliance (e.g. double dose). A multiplexor may be used to combine many compartments' state into a smaller number of lines. Other methods of detecting and transmitting compartment status exist and are within the scope of this disclosure despite not having been described. Multiple sensors may exist for each compartment. Multiple sensors may exist for each sub-compartment. The multiple sensors may provide redundancy (more than one method to detect compartment was breached) and/or the multiple sensors may provide different measurements such as temperature and breach detection.

A compartment opening event might also be detected using a wireless sensor. The wireless signal might be an impulse that is detected by the communication module or it might be a modulated RF signal. The modulation itself might encode the data, for example, the frequency indicates which compartment was breached. Each compartment might have its own radio such as RFID, NFC, ANT, BT, BTLE, Wi-Fi, cellular, 802.15.4, or other standards-based radio or a proprietary radio to communicate wirelessly either to another component on the system or to an external device. A solar cell can detect light upon opening a compartment. A pressure transducer may detect both environmental changes and the opening of a compartment, including air pressure changes and pressure due to the extraction of the medication.

Capturing Usage Activity when not Connected to Wireless Network

To anticipate circumstances where normal digital communications is not possible (possibly due to hardware failure of the communication module, failure to link to a communication module, hub or manifest server), visual compartment identifiers can also be used to help document the activation and compartment opening events. In one embodiment, the internal bottom surface of each compartment of the packaging body is marked with an id (e.g. a numeric value) in a color highly contrasting to the color of the package body. Alternately, the top of each compartment may be colored, numbered, bar-coded or otherwise labeled. In case of communication failure, which prevents the normal transmission of sensor event data (i.e., compartment opening) to the communication hub, the user will be notified that the event has been missed and to take a digital photo of the packaging and forward via email, text message or other digital mechanism to visually record the number and location of each open compartment. These messages are customized based on parameters stored in the digital packaging manifest, profiling the actions to be taken when scheduled sensor events notifications are not received. For example in the case of an older patient without smart phone access or skills, the system may take action to call the user or notify a caregiver directly. Alternately, the smart lid monitors, records, and stores event information such as compartment opened along with date &time locally. When a link to the communication hub is available, the smart-lid forwards the stored data, including any updates to the manifest, rules, etc. to the communication hub. In the event that the link to the communication hub is operational, but a connection to the server is not available, the application on the communication hub implements an analogous store & forward solution for when the connection to the server is again available.

The sensor-enabled packaging can also capture and record the qualitative characteristics of specific sensor-related events. For example, the remote monitoring server, using data parameters stored in the sensor event notifications, has the ability to distinguish whether the processing unit was able to record the real-time opening of an individual compartment within a sensor-enabled package versus relaying an opening event recorded while the system was not actively connected to the system's wireless connection (could use digital clock, elapsed time measurement, etc.). By using the manifest events log stored in the manifest repository to analyze the usage and transmission event patterns, caregivers and other responsible third parties can troubleshoot the user's communication or wireless connectivity environment.

An on-board temperature sensor, perhaps using a thermistor or thermocouple, allows the system to monitor temperatures and ensure that the temperature stays within the ranges allowed for each medication listed on the manifest. The lid may be provisioned with the temperature limits or it may automatically search for the limits based on the contents of a manifest, using either a smart device as a communication hub, using another device as a hot-spot for Internet connectivity, or making a direct connection to the Internet. Single-use temperature sensors that trip when the temperature exceeds a limit may be used and the state change is detected by the lid's CPU. Other environmental sensors such as shock, humidity, light, and pressure may also be included. If environmental conditions violate safe handling rules for the medication or vaccine, then the user is notified to this issue. Separately, other stakeholders such as the sender of the package may be notified to send a replacement.

Communication to the Manifest Repository

Figure 3:
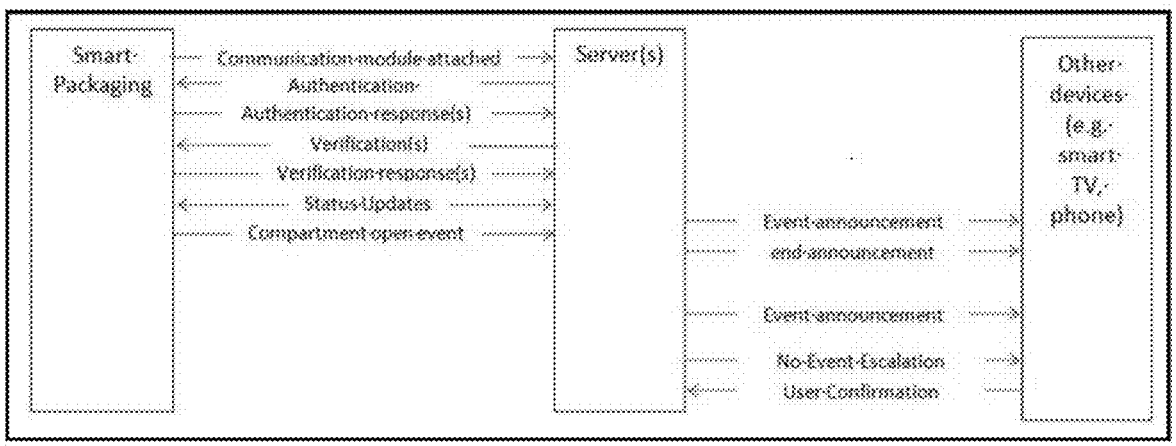
FIG. 3 is a sample sequence diagram illustrating bi-directional data flow between smart packaging, servers, and other devices.

As shown in FIG. 1 and FIG. 3, the SEP's communication module transmits event, status and activity data from the sensor-enabled packaging to a communications hub. This communication hub could be any new or existing device such as a cell phone, computer, tablet, television, set-top box, smart-watch, automobile computer or other electronic device capable to receiving, processing and transmitting data from the communication module. As described earlier the communication module can also be equipped to act as a communications hub.

The servers exchange data with the sensor-enabled package's communication module using the communication module and a communication interface. With sufficient bandwidth, this interface can support real-time communication; when sufficient bandwidth (including no connection) is unavailable, a store and forward communication model is used to ensure data integrity. Stored transactions are forwarded on to the remote servers when the communication link is re-established and the data exchanged can be acknowledged. Data may be retained at any stage in the communication process using a store-and-forward model to ensure that the data is successfully received by the server; data may be kept at each of these stages until an acknowledgement is received from the server. The shared communication interface will support the collection of a wide variety of transaction data parameters (e.g. validated time-stamped parameters, date, time, opening sequence, etc.) describing the sensor event transactions and usage data collected. In one embodiment of the invention, once the sensor-enabled package has been activated, the communications hub can communicate bi-directionally with the sensor-enabled package via the communication module to either forward data or receive updated software, manifest data, notifications, etc.

In order to transmit data from the package to the manifest repository server(s), the communication hub can support one or more communication protocols and physical interfaces such as IP, IPV6, Wi-Fi, Cellular, LAN, WiMAX, or other future forms or standards for digital communication when forwarding packaging event data to the manifest repository.

In one exemplary embodiment, the cloud-based communication server coordinates the bidirectional distribution of system messages, notifications, feedback and other system-generated communication relating to the user's specific local digital environment. System messages, notifications, feedback and the like are annunciated at the communication endpoints within a user's digital environment; these could include any combination of the following components: computer display, video or digital television screen, lighting system, audio device, wearable digital technologies, watches, tablets, or future technologies that can be prompted by the system. For example, the system could utilize a digital multimedia receiver (e.g. Apple TV, Xfinity cable box, etc.) to superimpose a system notification screen or message bar onto the primary media monitor that would progressively cover a larger portion of the screen until the desired sensor-enabled packaging event was triggered and the corresponding message was received from the remote manifest repository. A key capability of the system involves translation and delivery of notifications, user information, programmatic information requests from paired devices and other automated tasks described in the associated rules sets.

As shown in FIG. 1 and FIG. 3, the communications server communicates bi-directionally with the remote manifest repository server to coordinate the transmission and reception of events from the sensor-enabled packaging and the rules and parameters stored in the digital packaging manifest which are stored and managed within the manifest repository server. The cloud-based communications server can also report the status of the sensor-enabled packages, their compartments, hardware status, etc. concurrently with messages sent to the remote manifest repository. In a perfect state, the communication module is able to make timely connections (through a communication hub) to the cloud-based server with minimum network latency 24 hours a day. Using this status data and comparing when system activity was generated versus delivered as digital communication, deviations from the expected pattern of compartment openings or persistent network latency indicated by higher than expected off-line reporting (possibly due to unreliable network connections) usage events can indicate larger problems with the usage environment. These data trends could trigger not only user notifications but provide trend data that prompts a local caregiver to investigate the systematic reason for the anomalies (deteriorating mental state, faulty communications environment, etc.) and take corrective action.

Limiting e-PHI and PII communication with external devices to only include an encrypted GUID allows communication that is void of any personal information. In a non-limiting example, only the secure database has the private key required to extract the plain-text GUID and only the plain-text GUID can be used to match a particular manifest to a user. This solution allows for secure end-to-end communication without burdening the entire system with the need for an encryption/decryption engine. It is possible to also install an encryption engine in the lid that provides, for example, AES encryption, including a solution that verifies the integrity of the encryption engine at each system start. The encryption solution may meet the requirements of FIPS 140-2 (or subsequent version). A secret GUID may be used in much the same way 802.11 (Wi-Fi) WPA2 uses a pre-shared key to encrypt data. Other forms of end-to-end encryption for the entire data stream are possible. As examples: TKIP, DES, DES-X, UES, triple DES.

Communications Server, Remote Server and Manifest Repository

As shown in FIG. 1 and FIG. 3, the sensor and user invoked sensor communication is transmitted from the local communication hub using standard network and transaction protocols to the remote communication server. This server provides system security, validates incoming and outgoing communication types (system notification, sensor event, manifest update, user profile log-in, information request, etc.) and manages the routing of the transaction to the appropriate user device or communication gateway. Depending on the nature of the communication, the digital communication is sent to the manifest repository, which manages the security, creation, provisioning information, activity event logging, usage rules, information access rules and encryption, data visualization, data archiving and other data management activities required.

Digital Packaging Manifest

As shown in FIG. 2, and discussed earlier, every sensor-enabled packaging lid is permanently associated with at least one unique identifier that is permanently associated with the digital packaging manifest. The person or organization provisioning the sensor-enabled packaging completes this digital manifest profile. In some cases, it may be the consumer who has purchased the packaging and is taking responsibility for provisioning their own contents (i.e., medications) and will have total control of setting the rules, permissions, security levels and all other parameters for that specific manifest and associated sensor-enabled package. In other cases (e.g. pharmaceutical trial or sponsored health program), the user might agree to comply with a set of usage or adherence rules involving the monitoring provisions in exchange for some benefit, such as reduction in medication prices or opportunity to participate in a drug trial. Within either scenario, the user's cooperation and consent is a base requirement for this form of monitoring to be successful.

Packaging Identification

The first step is to log into the provisioner's personal account. First time users will be asked to set-up an account before being able to access the provisioning or other areas of the system. Users are always validated through a variety of secure methods. These could include but are not limited to passwords, biometrics, card keys, two-factor authentication, etc.

Once logged in, the user will use one of several methods to identify the specific sensor enabled lid to be used in provisioning of a specific package. The user can either manually input a series of external alpha numeric characters imprinted on the protective packaging cover, automatically capture this data by means of digital photography, barcode translation, NFC, RFID, BT Smart, magnetic strip or some other unique external identifier. Once captured, the external data will be processed using a computing device (e.g. smart phone, tablet, computer, etc.). Under all circumstances processing the externally readable identifier will direct the user, via a software application or web interface, to the remote server and the digital manifest repository to notify the digital manifest repository that the provisioned package has been activated.

Provided the identifier has been accurately relayed to the digital manifest repository (no errors in manual input process or bar code capture), the repository uses the package's external identifier to load, for provisioning or modification, the blank packaging manifest that was created when the sensor-enabled packaging lid was originally manufactured. (Alternately, the manifest may be created when a new package external identifier is sent to the server as part of the SEP provisioning process). The external alphanumeric identifier is only a human readable reference to allow a user or interested party (first responder, relative, someone who found a lost package) to match a specific package to a specific manifest. The digital identifier embedded into the chip fused into sensor-enabled lid/docking station is completely different and cannot be derived by any external identifiers or codes. Identifying and launching for modification the digital packaging manifest is the first step in the provisioning process.

Once the appropriate manifest has been identified, the user will be asked to provide password or biometric confirmation of the user's identify. If the user can be identified, the system moves on to the next steps to populate, edit or replicate a manifest.

Initiating the provisioning of a digital packaging manifest is much like a typical consumer retail transaction/relationship that provides a software process to collect various data parameters profiling the user and establishing access and security protocols. Depending on the use case (e.g. consumption of over-the-counter medications pre-packaged in sensor enabled packages), the user may not be required to provide personally identifiable information. If, on other hand, they wish to establish a recurring user relationship to support an on-going account relationship, the user may choose to include more personal demographic information and/or a more complete description of the digital environment (described earlier).

In addition to standard demographic data, this personal profile information could include information regarding the person or entity provisioning the sensor-enabled package, profile information on the recipient of the package, caregivers, shipping information, and emergency access privileges. In one embodiment of the invention, the packager could give first responders secure access to the digital packaging manifest to assist in rendering emergency care.

Once the generalized demographic data has been gathered and stored, the user provisioning the package will be asked to profile the contents being enclosed in each compartment (assuming they are not consuming commercially pre-packaged medications). Since the digital manifest was created when the sensor-enabled lid was manufactured, the manifest was pre-configured with the correct number or data entry fields for compartments supported by that specific lid. In one embodiment of the invention, the software interface displays a visual representation of the packaging body that assists the user in documenting the locations containing the actual contents. In an alternative embodiment, identifiers may be imprinted at the bottom of each well to help users identify the orientation of individual compartments.

Package Provisioning Steps

Figure 10:
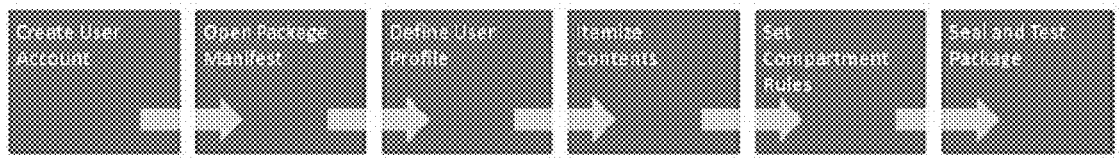
FIG. 10 depicts examples steps used to create, provision and manage a digital manifest.

In one embodiment of the invention the provisioning steps outlined in FIG. 10 summarize the process of provisioning the package with the appropriate contents. All reference to passwords, unique identifiers are based on the descriptions of these elements described elsewhere in this provisional patent.

Package Identification and Macro Profiling:

This series of steps outlines the minimum steps necessary to properly identify and prepare a specific package for provisioning.

1. Launch software application on computing device to begin process and authenticate yourself
2. Open packaging provisioning feature in application
3. Capture and verify the unique ID/Guid for packaging lid or docking station. Some options listed below: a. Barcode translation based on image capture and translation of unique ID/Guid b. Cable connection to baseplate, connector tab, or wireless connection to digitally identify unique ID/Guid c. Manual entry of unique ID/Guid into application interface 4. Confirm the digital packaging interface representation of the compartments layout matches actual packaging lid configuration
5. If application validates the package's unique ID/Guid, user proceeds to register package and completes the manifest's macro-data profile
6. To register the package and its manifest the user can choose to use a stored packaging template manifest profile or create a new manifest profile
7. For creating new package profiles you would collect the following data authentication and communication parameters: a. Communication ID's (e.g. Prime Link ID's, Hub ID's, Cell phone ID's, etc.)

b. Passwords/Trusted parties c. Records and data access privileges d. Identify "Provisioner" (e.g. relative, pharmacy, caregiver, facility) packaging the contents e. Usage events and data routing instructions (who receives the data)

f. Shipping and delivery parameters

8. Runs digital quality control check (is the lid circuitry, battery, etc., in working order)
9. Interface allows user to establish macro rules governing this individual package Provisioning Each Compartment or Sub-Package:

Once the package has been identified and validated, the user proceeds to associate specific items or contents with specific compartments or sub-containers using the add items function in the interface. Other features activate as necessary depending on the selections or choices the user makes when completing the manifest 1. User will be asked if they wish to populate the compartment based on an earlier stored template. If not, user will populate compartments with content data.
2. Using the add item feature click on the first compartment from interface representation 3. Screen will alert the user that they are about to add items to the first compartment in the package and make the proper indication in the screen rendering of the package layout 4. User will select mode for data acquisition or input (bar code, manual data entry, voice, etc.) or utilize the type ahead function that can match or verify specified drug names against the Federal Drug Administration's (FDA) Open FDA drug information database. a. If bar code is selected—use smart phone camera to read the FDA barcode on outside of pill bottle b. If using type ahead feature, begin typing until correct alternative appears 5. When all drugs have been identified and added to the first compartment's contents list users confirmed the process completed. At any point the user can select any drug added to the compartment list and expand the window to see more details on the drugs stored in the OpenFDA database, including but not limited to drug interactions, co-morbidities, dosages, pictures of the pill, etc.

6. Once the first compartment profile complete? Yes/No. User is provided option to replicate contents list for next compartment 7. Optionally, each compartment can also be checked for drug warning or incompatibilities as the user confirms process completion 8. Users confirm search results matches, (check dosage, pill color, etc.)

9. User edits each item profile as necessary for accuracy

10. Next compartment is automatically displayed until the user determines the package is completely provisioned Creating Rule Sets Governing the Compartments/Sub-Packages and or their Contents Once the user either completes the provisioning of each compartment (in some cases the user may choose to leave unneeded compartment empty) rules can be associated with each compartment or sub-package. If the user has chosen to use a packaging profile template, these data elements might be pre-populated in the manifest. If not, the user would assign rules to govern their usage. The usage rules assigned to each compartment or sub-package can reference or be governed by any event or data parameters that can be sensed, derived, inputted, or stored within the manifest. The step for creating and assigning rule are outlined below:

1. Select package compartment from the interface representation in the application interface 2. Create compartment usage rules=>Application presents rules profile window with options. An example rule might use a triggering event (such as the opening of a compartment) to initiate a series of action or measured responses. Actions could also be triggered if anticipated events don't happen as expected. These could be tied times, dates, hardware statuses and other sensory inputs all of which can be used separately or in combination to describe the conditions to trigger actions on the part of the system. These actions are guided by the available communication options outlined in the manifest profile (phone, text, watch, screen in screen on TV, etc.).

3. Once a rule is constructed and associated with a specific compartment or sub-package, escalation procedures/protocols, secondary messages, drug recall messages notifications, data feeds from hardware devices, etc.

4. Use compile rules into summary and render in a confirmation display

5. User accepts or modifies rule set for each compartment

Seal the Package and Execute Quality Control Check

Before distributing the final package to a user, it is important to verify that the fully provisioned package has not been damaged in the process and that each compartment's or sub-package's sensors are operating correctly. To satisfy this requirement the user needs to seal the finished package and test the finished package to confirm its state. In one embodiment of the invention these steps include:

1. Remove the layer of protective adhesive or sealant has been applied to the underside of the sensor-enabled packaging lid or the upper horizontal lip surface of the packaging body. To ensure each sensor-enabled packaging lid align with the specified packaging body compartment openings when permanently mounted, the packaging body is configured with alignment holes or posts to assist in properly sealing of finished packages.)

2. Attach lid to compartments

3. User presses firmly to ensure an effective seal.

4. User uses communication module or cable connector to test the sensor array/circuits and other elements of the provisioned and sealed package.

5. Once tested the user designates the package as sealed tested in the manifest

Auxiliary Usage Instructions

Under certain circumstances it may be necessary and useful to include usage information with the sensor enabled package. Once completed the manifest has important information regarding how the contents should be used. Of course, this information is always accessible if you have access to the manifest which is available to any user via the unique identifier associated with each package. However, there are circumstances where this information would be more useful if it were physically printed on the lid or included as a printed informational insert and delivered to the user with the sensor-enabled packaging.

In one embodiment of the invention the sensor-enabled lids could be feed through a printer so identifiers, dates, icons, instructions and other visual cues could be printed either over the compartment openings or on other pre-designated areas to support proper usage. The method of printed support could also be integrated into high volume production environments where manufacturers have decided to pre-package the contents into sensor-enabled packaging. In this use case scenario, the manufacturers could decide to not only print customized instructions and information of the outer packaging, but also pre-populate data fields and other manifest parameters as part of the packaging process.

Alternate Workflows

Other steps for alternate workflows may be included as well as additional detail in the steps described. For example, if the system has no outside data connection, it might simply store events and associated meta-data and/or usage activity data, such as compartment number, GUID, date, time, rules engine updates, annunciations, and the like and forward them later. Supporting a real-time clock that may be provisioned at the time the lid is manufactured, or at a later date such as when the lid is provisioned or when it is first opened, is one method of enabling time/date-stamping functionality. The lid may make a connection to an external device, such as an NTP server, via an IP connection for example, or it may make a connection to another device such as a smart phone/watch and use that device's date and time. Location may be used to compensate for travel and provide input for the rules engine to adjust medication intervals for time zones during travel. Location can come either from a local GPS solution, by provisioning, or by query to an external device such as a tablet or PC. Smart pills may be used that can communicate with the system to confirm they have been ingested. Combining the location the pill was removed from the pack with the time it was ingested helps verify that the proper person ingested the pill.

Data may be analyzed to determine efficacy, for example, does user non-compliance such as taking a medication early/late have a measurable effect? This is particularly helpful if some related physiological inputs are included. The inputs might be, by non-limiting example: weight, blood glucose level, heart rate, blood pressure, oxygen saturation level, ECG, EEG, spirometry output, images of, for example, the fundus or wound, saliva and/or breath analysis to detect, for example, ketones and proteins, blood chemistry tests to detect sugar, hormone, and electrolyte levels.

Compartment Provisioning

In the case of medications and medical contents, it is critical that contents are correctly identified. The software process will support multiple data entry conventions to ensure use of the most convenient and seamless process to accurately document the contents of each compartment. These could include, but are not limited to, keyboard entry, bar code reading, importation of e-prescription information or standardized HIPAA electronic data interchange transaction, speech to text, importation of drug profiles from national prescription drug labeling repository, digital camera, etc. The contents profile of each compartment can contain individual profiles of items included in the content. In one embodiment of the invention, users can use a graphical user interface to query information (name, dosage, manufacturer, visual image tablet or device, national medication ID number, etc.).

Packaging Rule Set Creation

Once a user is satisfied with the provisioning of the contents of each compartment, the user is prompted to create packaging compartment usage profiles. These define a set of consumption schedules, actions, notifications, communication rules, priorities, escalation steps, access privileges, and other data parameters necessary to govern the management of the overall package and its individual compartments. In one embodiment of this invention, the usage parameters recorded in the manifest can also be pre-set for a company that distributes over-the-counter medications, pre-packaged in sensor-enabled packaging and wishes to gather voluntary usage information. In this usage case the usage and data privacy parameters could be presented in a form (similar to End User Licensing Agreements) that requires user consent before a wireless connection could be initiated and usage data exchanged. In one embodiment, the end user would authorize the pharmacy to provision the package. Profiles may be templated. For example, if the drug is to be taken every 8 hours, this is already known from the prescription and may be presented for the provisioner to confirm. Once the user takes the first pill, the template is activated with that start time. The individual responsible for creating and maintaining the manifest has control for establishing, maintaining and changing this third party data exchange rule set; in addition to initial set up, this individual also has the ability to refuse data access to any previously allowed outside parties and redirect or eliminate routing of information affiliated with the manifest. The rules set can be configured to define the preferred methods (phone, fax, television, email, etc.) for the eventual routing or mirroring data or alerts via the communication gateway to any verified, interested parties (e.g. physician, insurer, etc.). Individual control over these data streams enables incentive programs and business relationships.

Sensor-Event Mechanism that Triggers Outside Processes

In one embodiment of the invention thresholds and event triggers can be set that prompt activation, updating, communication or data collection via other sensors, devices, software applications, system processors, prompted manual data entry, image processing, etc. These thresholds and triggers are set in the digital manifest and can be associated with the usage activity associated with the sensor-enabled packaging.

As an example, a prescription of a diuretic for a post-operative cardiac patient may trigger the collection of patient weight information. In the case of patients participating in clinical trial for sleep disorders, creating a threshold tied to the consumption of the medication being studied which trigger a data stream from a sleep monitoring device can give researchers a much better idea of the impact their medication is having. The same situation would apply to medication for high blood pressure, diabetes and other conditions where it is useful to request additional data from third-party sensors or devices that can be queried as a result of a trigger stored in the digital manifest.

In another embodiment, the system may be set to remind the user to take a special event medication (e.g. refrigerated medications such as Amoxicillin), complete with customized alerts that take into consideration special requirements (e.g. the need for refrigeration).

Sensor-Enabled Packaging Lid Testing

The final optional step in the provisioning process is to use a local provisioning device (smart phone, computer etc.) to test sensors controlling the integrity of the sealed compartments, battery, and other functional components of the provisioned package using a wireless or cable-based version of the communication module. If quality tests are used and the provisioned package passes these passive quality control tests, the package can be declared provisioned and inspected. The package and its content are now ready for distribution.

It is envisioned that any of these steps could be replicated as processes within an automated provisioning, manufacturing packaging or distribution process.

Manifest Provisioning, Usage and Management Software

Control software will govern the creation and management of digital packaging manifests following rules and processes similar to that described in FIG. 10. The software works in tandem with a remote server and the construction of digital packaging manifest, using various methods of user interface and or programmatic techniques, it utilizes an application programming interface to automate the process of creating pre-packaged medications. This capability requires the creation of a manifest that can be programmatically automated in such a way that commercially packaged medications could be packaged, while the manifests governing their usage are automatically configured and associated with, and recorded in, a digital manifest.

This model of commercial packaging could also utilize a system of software and digital authentication tools to automatically link the wireless communication module. The wireless communication module, when re-issued to different people, as in a hospital for different patients, may have a unique identifier that is different from the GUIDs in the SEP. Based on the communication modules' unique digital identifier, the system may automatically link the communication module to the sensor-enabled packaging and, if necessary, to a particular communication hub, for example, a smart phone. This would enable the high-volume packaging of medication regimens to be delivered to assisted living centers, hospitals, or other locations where it is valuable to utilize automated packaging systems to service high volume customers involved in servicing end users. When the SEP is created and when the wireless communication module is provisioned for a user, each action results in updates to the servers to help ensure proper distribution of products. For example, an exception may be generated if an SEP created for one entity connects to a communication module provisioned for a different entity.

Leverage the Digital Manifests to Create Auction Marketplace

By utilizing a disposable packaging paradigm, this invention, leveraging its digital manifest-based methodology, allows for the facilitation of various innovative commercial transactions and reward/incentive systems. Because the digital manifest(s) creates a unique information aggregation point, this creates a reference point upon which a user can facilitate the purchase and reordering of the contents described in the manifest.

In one embodiment, when used to support the provisioning of pharmaceutical products, the digital manifest may, in reality, be the only point in the prescription and medication consumption cycle that records a definitive list of all drugs (sourced via multiple doctors and pharmacies) being taken by a specific patient. In addition to the clinical and safety benefits of cross-checking possible drug interactions, our digital manifest could also act as the basis for an individual responsible for the manifest to take advantage of best price comparisons. This could be done by automating the process of converting this manifest information into requests for pharmacies and other certified drug distributors to bid for the fulfillment of these orders.

To facilitate a best price comparison, the entity or person responsible for the digital manifest will simply offer the drug regimen described in the manifest(s) as an anonymous request for pricing from various drug suppliers, who, in effect, bid on supplying the drugs provided in their specific drug regimen. The terms of the transaction would be based on mutually agreed upon purchase conditions (e.g., providing fulfillment houses the opportunity to bid on generic, multiple month or other filters that might be applied). As with other efficient markets, the seamless nature of matching buyers and sellers would work to reduce the overall cost of supplying mail order medications.

Accumulated Usage Events Enable Big Data Analysis

Through data aggregation, the manifest data accumulated allows big data analysis to support retrospective and prospective analyses. These analyses serve to detect adverse or beneficial drug interactions. They enable better understanding of long-term effects of drug use and support longitudinal studies. By supporting user feedback, such as "nausea," "sleepy," "odd-taste," and/or interfacing with physiological measurement systems that provide data including: weight, blood pressure, heart rate, blood glucose levels, physiological variability, respiration rate, the collection of digital manifests usage/feedback/physiological parameter data becomes a rich data source from which to learn. The analyses can also be used for A-B testing of different form factors, software features, and annunciations to determine which lead to the best compliance rates. Similarly, different educational segments that are transmitted to the patient's interface device as a function of compliance rate and drugs prescribed can be test. The patient, for example, may request educational segments when a patient is curious to know more about a prescribed drug. Information may be acquired via access to web-based resources such as openFDA. Targeted ads may be provided to the user based on activity, drug regimen, compliance rates, and the like. These ads may be displayed on a smart phone, smart TV, PC, streaming media (such as Amazon Video) or on a conventional TV. Access to the de-identified data, analysis results from data studies and the like may be sold as services. The unique ID on the sensor-enabled packaging helps verify the integrity of the data used in these sorts of analysis.

Environmentally Safe Medication Recycling

The one-time use nature of each sealed package, and its ability to record the provenance of the enclosed contents within individual compartments, allows this invention to document, via its activity log, both the package's usage and management activity, and also the potential recycling and environmentally correct disposal of its contents. This capability provides much broader and detailed records of the usage of the packaging and its compartment containers through the full usage cycle of the product. The invention therefore enables the "provisioners" responsible for distributing these medications the capability to support a pro-active recycling program—including financial incentive.

Based on the unique identifiers and detailed manifests associated with each package, the mechanism exists to offer financial or social incentives to encourage users to return used packaging with any unused quantities of medications. In this system, bar coded return packaging would be used to provide a free mechanism to ship and validate the return of potentially dangerous drugs for proper disposal. Each returned package would be tested against its original manifest to confirm which compartment(s) remain sealed.

A financial incentive could be earned based on the level of consumer engagement. For anonymously returned medication there might be a minimal reward, while sharing more demographic detail might boost the potential value of any specific package return. This system could also work well for the return of inadvertently lost medications.

Figure 11:
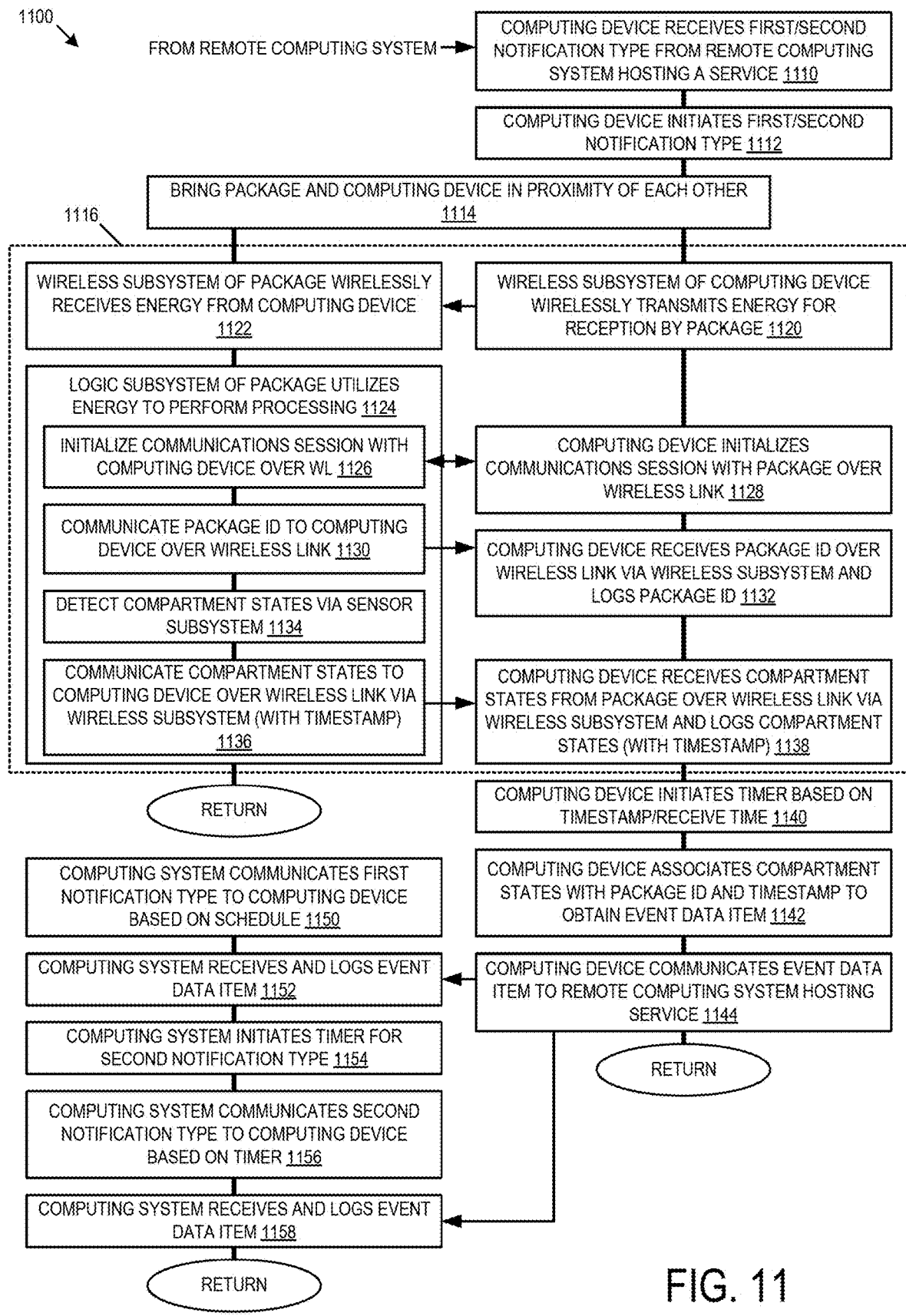
FIG. 11 is a flow diagram depicting an example method associated with a packaging system having a wireless interface between a sensor-enabled package and a communication hub.

FIG. 11 is a flow diagram depicting an example method 1100 associated with a packaging system having a wireless interface between a sensor-enabled package and a communication hub. Method 1100 may be performed using the example sensor-enabled package of FIG. 5 in combination with another computing device such as a special-purpose communication hub or a mobile device (e.g., smart phone), as a non-limiting example.

By using the smart phone or other suitable computing device, a "state" of the package's compartment (e.g., which circuits are opened or closed at any moment in time) may be determined before a patient opens the next scheduled compartment. After the computing device confirms recording a valid package status snapshot from the NFC/RFID chip, the computing device can coordinate with a cloud-based service to report a before and after snapshot of the compartment states surrounding a time when a compartment was opened by a user to access a medication. Based on whether the reported data conforms to scheduled expected usage patterns, the service may prompt the user to take their medication. Notification/reminder messages may be used let the user know if there are any actions they need to perform, including whether before and/or after measurements of compartment state need to be obtained.

At 1110, the computing device receives a first notification type from a remote computing system hosting a service. The first notification type may take the form of an initial notification that includes a reminder to take a medication. In at least some implementations, the remote computing system and/or the local computing device may communicate and initiate the first notification type based on a predefined medication treatment schedule. At 1112, the computing device initiates the first notification type, for example, by displaying or otherwise outputting a message or other audio/ visual/haptic indication. Alternatively, the first notification type may be generated at the computing device without receiving the first notification type from a remote computing system.

At 1114, a user brings the package and the computing device in proximity to each other to enable communications and/or power transfer over a wireless link between the two devices. For example, an NFC and/or RFID chip of the package may be inductively powered by the computing device rather than including an on-board power source. A non-limiting example of a suitable NFC chip is model LPC8N04 microcontroller manufactured by NXP™, which is wirelessly powered from the NFC field. However, other suitable chips or hardware components may be used. At 1120, a wireless subsystem (e.g., of a communications subsystem, input/output subsystem, and/or power subsystem described in FIG. 24) of the computing device wirelessly transmits energy for reception by the package. At 1122, a wireless subsystem (e.g., of a communications subsystem, input/output subsystem, and/or power subsystem described in FIG. 24) of the package wirelessly receives energy from the computing device.

At 1124, a logic subsystem of the package utilizes the energy received from the computing device to perform a processing pipeline, which includes one or more subprocesses. An example logic subsystem will be described in further detail with reference to FIG. 24. At 1126, for example, the logic subsystem of the package initializes a communications session with the computing device over a wireless link, and the computing device initializes the communications session with the package over the wireless link at 1128.

At 1130, the logic subsystem of the package communicates a package identifier to the computing device over the wireless link via the wireless subsystem. The package identifier may include any of the various identifiers disclosed herein, including hardware and/or software-defined identifiers that are unique with a particular domain (e.g., globally unique). At 1132, the computing device receives the package identifier over the wireless link via the wireless subsystem, and logs the package identifier.

At 1134, the logic subsystem of the package detects compartment states of its on-board compartments via a sensor subsystem. At 1136, the logic subsystem of the package communicates a set of compartment state data indicating the compartment states to the computing device over the wireless link via its wireless subsystem. Each compartment of the package may have an identified compartment state—e.g., opened or sealed. The compartment state data communicated by the package may be accompanied by a timestamp representing a time at which the compartment state data was measured or obtained.

At 1138, the computing device receives the compartment state data indicating the compartment states from the package over the wireless link via its wireless subsystem and logs the compartment states with a timestamp. The timestamp logged at 1138 may correspond to the timestamp communicated by the package or a receive time of the compartment state data.

At 1140, the computing device initiates a timer based on the logged timestamp. The timer may represent a pre-defined time value (e.g., 10 minutes) for which the processing pipeline 1124 is again to be performed to obtain a subsequent set of compartment state data. In at least some implementations, responsive to the timer attaining the pre-defined time value, the computing device may locally initiate a second notification type, such as previously described at 1110/1112 for the first notification type. The second notification type may include a reminder for a user to perform operation 1114 to initiate operations 1116-1144 to obtain, log, and report a subsequent set of compartment state data or a subsequent event data item.

At 1142, the computing device associates the compartment states with the package identifier and the logged timestamp to obtain an event data item. Alternatively, the compartment state data may be communicated by the package with the package identifier. The event data item may represent a first of two event data items that collectively provide a bracketed consumption event with respect to the contents of the compartment(s). The event data item may be stored locally at the computing device where it may be later processed, displayed, or otherwise used by the computing device. Additionally, at 1144, the computing device may communicate the event data item to a remote computing system hosting a service, which may refer to the computing system/service that initially communicated the first notification type that was received by the computing device at 1110, as indicated at 1150, for example.

At 1152, the computing system receives and logs the event data item, for example, by storing the event data item in a database system in association with one or more user accounts/profiles that are linked with the package identifier. Additional processing may be performed by the service at 1152 as was previously discussed with respect to the cloud services. At 1154, the computing system may initiate a timer for the second notification type. The timer initiated by the remote computing system at 1154 may be in addition to or as an alternative to the timer initiated at 1140 by the computing device. This timer may similarly represent a pre-defined time value (e.g., 10 minutes) for which the processing pipeline 1124 is again to be performed to obtain a subsequent set of compartment state data. In at least some implementations, responsive to the timer attaining the pre-defined time value, the computing system may communicate a second notification type at 1156, which may be received and initiated at the computing device as previously described at 1110/1112 for the first notification type. The second notification type may include a reminder of a user to again perform operation 1114 to initiate operations 1116-1144 to obtain, report, and log a subsequent set of compartment state data or a subsequent event data item at 1158.

While method 1100 of FIG. 11 is described with respect to a wireless link being established between a sensor-enabled package and a computing device, it will be understood that method 1100 or portions thereof may be performed over a wired link established between a sensor-enabled package and a communication hub via a pair of electronic interfaces.

Figure 12:
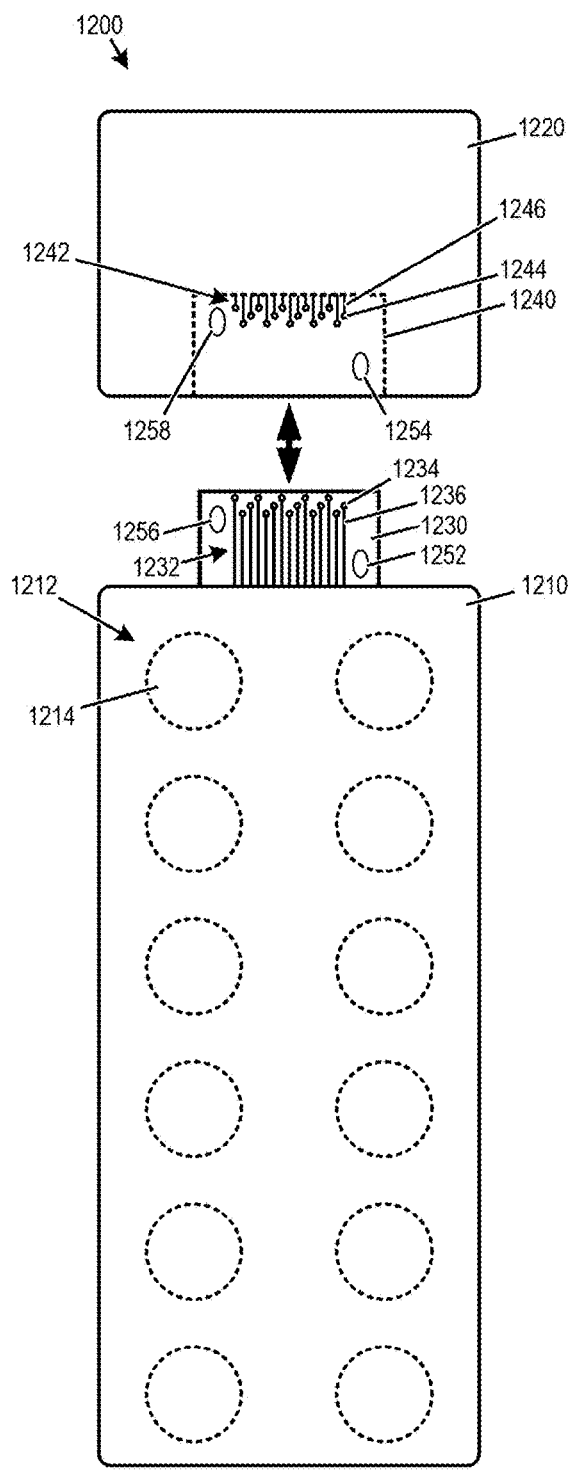
FIGS. 12 and 13 depict an example packaging system in decoupled and coupled configurations, respectively.

FIG. 12 depicts an example packaging system 1200 in a decoupled configuration in which a sensor-enabled package 1210 is physically and operatively decoupled from a communication hub 1220. In this configuration, an electronic interface 1230 of package 1210 is physically separated from an electronic interface 1240 of communication hub 1220.

Electronic interface 1230 of package 1210 includes a first set of electrically conductive pins 1232 of which pin 1234 is an example. Pins 1232 each form a terminal end of a respective electrically conductive path or electrical trace of which electrical trace 1236 is an example. In at least some implementations, pins 1232 may be organized into one or more rows, such as depicted in FIG. 12 or FIG. 7, as non-limiting examples. Electronic interface 1240 of communication hub 1220 includes a second set of electrically conductive pins 1242 of which pin 1244 is an example. Pins 1242 each form a terminal end of a respective electrically conductive path or electrical trace of which electrical trace 1246 is an example.

In the example depicted in FIG. 12, electronic interface 1230 of package 1210 takes the form of a connection tab as an example of a male-side connector, and electronic interface 1240 of communication hub 1220 takes the form of a connection port as an example of a female-side connector. In another example, electronic interface 1230 of package 1210 may take the form of a connection port as an example of a female-side connector, and electronic interface 1240 of communication hub 1220 may take the form of a connection tab as an example of a male-side connector.

Package 1210 in this example includes a set of compartments 1212 of which compartment 1214 is an example. Each of compartments 1212 may take the form of a sealed compartment formed by a tray portion and a lid or cover portion, such as previously described. Package 1210 may be referred to as a sensor-enabled package and/or a cover of package 1210 may be referred to as a sensor-enabled cover. As previously described, a state of each compartment as being opened or sealed closed may be sensed by measuring resistance, capacitance, and/or impedance of electrical traces that are associated with each of the compartments and/or their covers. These electrical traces may be in electrical contact with one or more of the electrical traces associated with pins 1232 and/or may traverse or terminate at a logic subsystem (e.g., microprocessor or other logic device) and/or power source (e.g., battery or induction antenna) located on-board package 1230.

Figure 13:
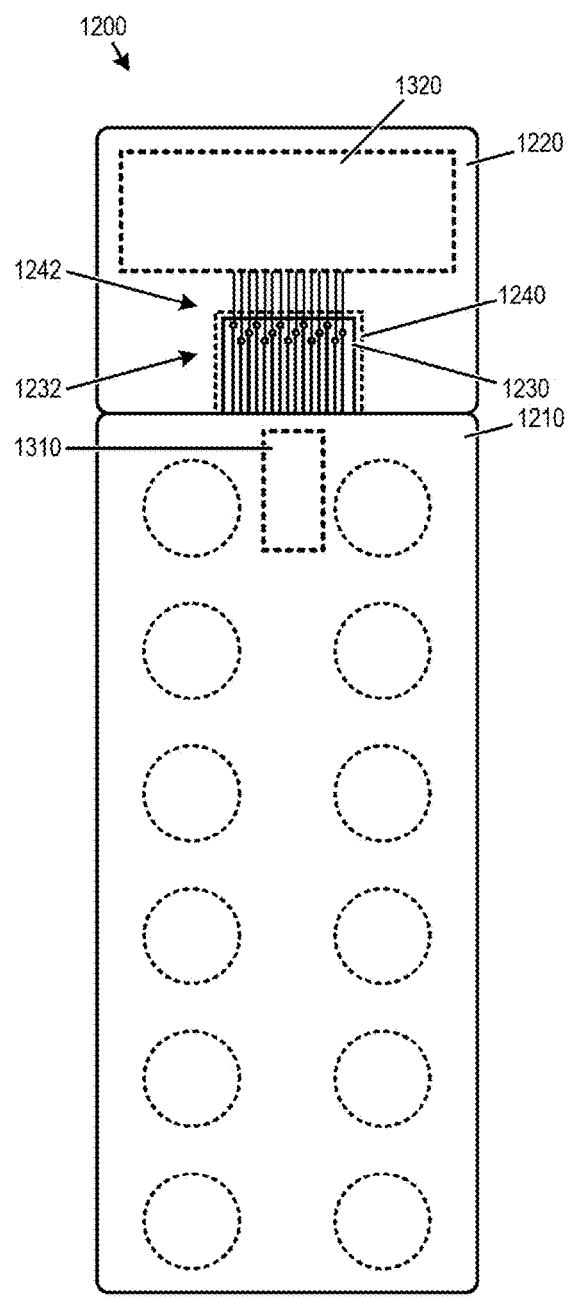

FIG. 13 depicts packaging system 1200 in a coupled configuration in which package 1210 is physically and operatively coupled to communication hub 1220. In this configuration, electronic interface 1230 of package 1210 is in electrical contact with electronic interface 1240 of communication hub 1220 via one or more pairs of pins 1232 and 1242, thereby enabling electrical power, ground reference, and/or data to be exchanged between package 1210 and communication hub 1220. For example, pin 1234 of electronic interface 1230 may physically contact or may be in electrical contact (e.g., via an intermediate conductor) with pin 1244 of electronic interface 1240. The exchange of electrical power, ground reference, and/or data may be bidirectional or unidirectional, depending on implementation and/or operating conditions. As described in further detail with reference to FIGS. 15-20, an intermediate conductor may be disposed between one or more of pins 1232 and one or more of pins 1242 to provide electrical contact therebetween. As an example, an intermediate conductor may take the form of a compressible, intermediate conduction layer.

In at least some implementations, package 1210 and communication hub 1220 each include one or more alignment structures that are sized and shaped to accommodate corresponding alignment structures of the other of package 1210 and communication hub 1220. In the coupled configuration of packaging system 1200, the alignment structures of package 1210 and of communication hub 1220 cooperate to ensure sufficient alignment of pins 1232 of electronic interface 1230 with pins 1242 of electronic interface 1240 to establish electrical pathways therebetween. In FIG. 12, for example, package 1210 is depicted including example alignment structure 1252, and communication hub 1220 is depicted including example alignment structure 1254. In a first example, alignment structure 1252 of package 1210 may take the form of an alignment post or protrusion, and alignment structure 1254 of communication hub 1220 may take the form of an alignment port or opening that is sized and shaped to accommodate alignment structure 1252 in the coupled configuration of packaging system 1200. In a second example, alignment structure 1254 of communication hub 1220 may take the form of an alignment post or protrusion, and alignment structure 1252 of package 1210 may take the form of an alignment port or opening that is sized and shaped to accommodate alignment structure 1252 in the coupled configuration of packaging system 1200.

An alignment structure, such as examples 1252 and/or 1254 may each have a non-symmetric or non-reversal shape that precludes electronic interfaces 1230 and 1240 from being physically and operatively coupled in an opposite orientation, thereby precluding pins 1232 from being electrically coupled with pins 1244 in an unintended or unsupported configuration. Additionally or alternatively, an alignment structure may be positioned off-axis or asymmetrically relative to a symmetry plane of package 1210 and/or communication hub 1220. For example, alignment structure 1252 is positioned on a right-hand side of a symmetry plane of package 1210, and alignment structure 1254 is positioned on a right-hand side of a symmetry plane of communication hub 1220 without symmetric alignment structures being positioned on a left-hand side of the symmetry planes in FIGS. 12 and 13. Package 1210 and/or communication hub 1220 may each include one or more additional alignment structures, such as alignment structures 1256 and 1258, respectively. These additional alignment structures may further support or enable alignment pins 1232 of electronic interface 1230 with pins 1242 of electronic interface 1240. Furthermore, in the example depicted in FIGS. 12 and 13, alignment structures 1252 and 1256 are not symmetrically positioned and shaped about a symmetry plane of package 1210, and alignment structures 1254 and 1258 are not symmetrically positioned about a symmetry plane of communication hub 1220 to preclude the opposite orientation of the coupled configuration. However, in yet another example, alignment structures may be symmetrically shaped and/or sized about a symmetry plane to enable at least two reversible coupled configurations for the packaging system.

In the example depicted in FIGS. 12 and 13, alignment structures 1252 and 1256 are positioned on or within a connection tab formed by electronic interface 1230 and flank pins 1232, and alignment structures 1254 and 1258 are positioned on or within a connection port formed by electronic interface 1240. However, alignment structures may be positioned on or within other suitable portions of the packaging system, including on or within portions that do not include electronic interfaces of the packaging system.

FIG. 13 schematically depicts electronic components 1310 of package 1210 and electronic components 1320 of communication hub 1220 that may be in electrical contact with electrical traces associated with pins 1232 and 1242, respectively. Electronic components 1310, 1320 may each include one or more of a logic subsystem, data storage subsystem, power subsystem, communications subsystem, and/or input/output subsystem, for example. Aspects of these various subsystems will be described in further detail with reference to FIG. 24, for example.

Figure 14:
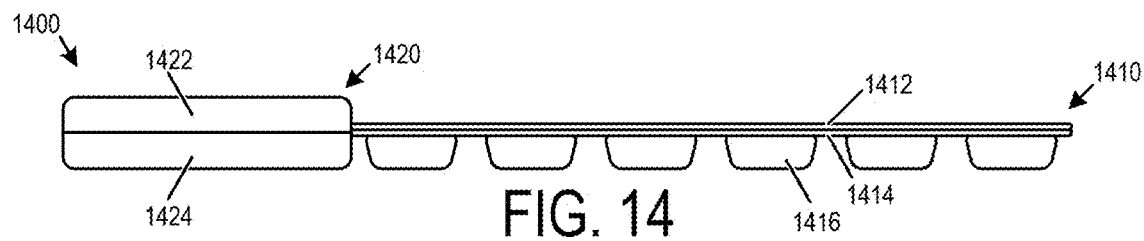
FIGS. 14 and 15 depict another example packaging system in a coupled and decoupled configuration, respectively.
Figure 15:
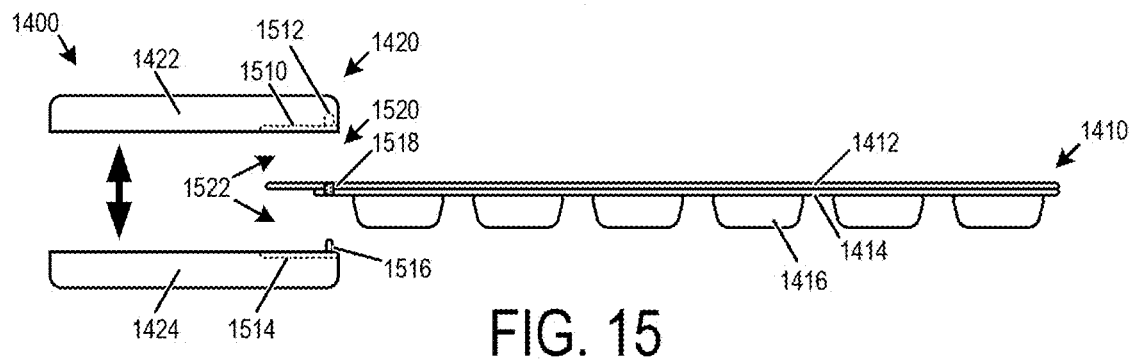

FIGS. 14 and 15 depict another example packaging system 1400 including a sensor-enabled package 1410 and a communication hub 1420. Packaging system 1400 is a non-limiting example of previously described packaging system 1200 of FIGS. 12 and 13 from a side view perspective. In this example, package 1410 includes a tray portion 1414 having compartments (e.g., 1416) that are covered or otherwise sealed closed by a cover or lid portion 1412.

FIG. 14 depicts communication hub 1420 and package 1410 in a coupled configuration, such as previously described with reference to FIG. 13. Further, in this example, communication hub 1420 is formed from an upper portion 1422 and a lower portion 1424 that may be joined to secure the communication hub to package 1410 in the coupled configuration. FIG. 15 depicts communication hub 1420 and package 1410 in a decoupled configuration, such as previously described with reference to FIG. 12. In FIG. 15, upper portion 1422 and lower portion 1424 of communication hub 1420 are separated from each other enabling package 1410 to be released from the communication hub.

FIG. 15 depicts an example of an electronic interface 1520 of package 1410 in the form of a connection tab, and an electronic interface 1522 of communication hub 1420 in the form of a connection port formed by one or both of recessed regions 1510 and 1514 of portions 1422 and 1424, respectively. Electronic interfaces 1520 and 1522 each include a set of pins, such as previously described with reference to FIGS. 12 and 13, for example. In at least some implementations, a second pair of electronic interfaces may be provided at an opposite side of the connection tab from electronic interface 1520 and at portion 1424 of the communication hub. Furthermore, in at least some implementations, an intermediate conductive layer may be disposed between electronic interfaces 1520 and 1522 as will be described in further detail with reference to FIG. 18.

FIG. 15 further depicts examples of alignment structures in the form of an alignment post or protrusion 1516 provided on portion 1424 of communication hub 1420, and an alignment port or opening 1518 formed within package 1410 that accommodates post 1516. Additionally, portion 1422 includes an alignment port or opening 1512 that accommodates a terminal end of post 1516 that passes through port 1518 of package 1410 to further secure and align portions 1422 and 1424 with the package. In the example depicted in FIG. 15, alignment port 1518 formed in package 1410 passes through both cover 1412 (e.g., a backing film) and tray 1414 to secure and align both portions of the package to communication hub 1420. In an example, tray 1414 may take the form of a thermoformed plastic tray. A backing film corresponding to cover 1412 can be torn away or pushed through to access the contents of the tray compartments. Portions of the film corresponding to individual compartments may be perforated, scalloped, or otherwise formed to break or tear along a boundary that corresponds to the opening of a compartment.

Figure 16:
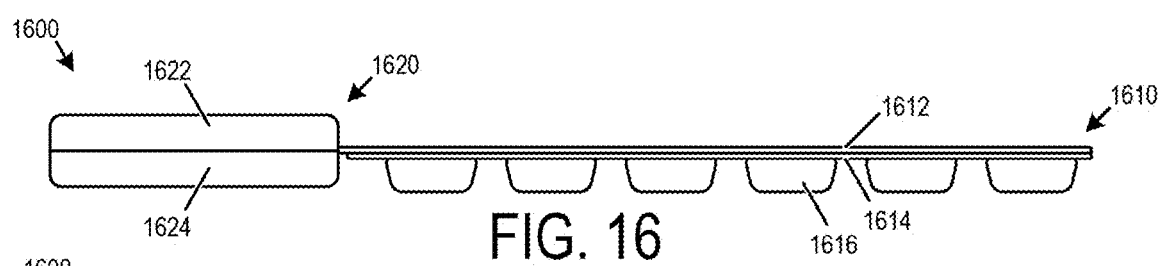
FIGS. 16 and 17 depict yet another example packaging system in a coupled and decoupled configuration, respectively.
Figure 17:
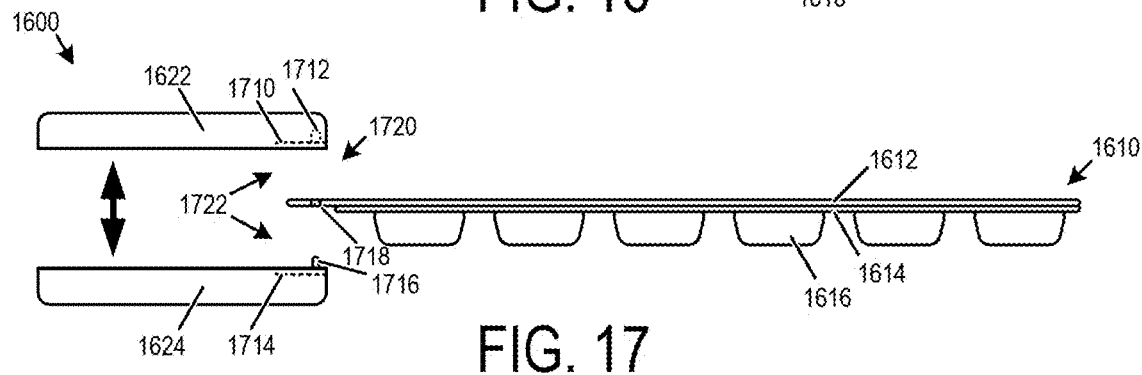

FIGS. 16 and 17 depict another example packaging system 1600 including a sensor-enabled package 1610 and a communication hub 1620. Packaging system 1600 is another non-limiting example of previously described packaging system 1200 of FIGS. 12 and 13 from a side view perspective. In this example, package 1610 again includes a tray portion 1614 having compartments (e.g., 1616) that are covered or otherwise sealed closed by a cover or lid portion 1612.

FIG. 16 depicts communication hub 1620 and package 1610 in a coupled configuration, such as previously described with reference to FIG. 13. Further, in this example, communication hub 1620 is formed from an upper portion 1622 and a lower portion 1624 that may be joined to secure the communication hub to package 1610 in the coupled configuration. FIG. 17 depicts communication hub 1620 and package 1610 in a decoupled configuration, such as previously described with reference to FIG. 12. In FIG. 17, upper portion 1622 and lower portion 1624 of communication hub 1620 are separated from each other enabling package 1610 to be released from the communication hub.

FIG. 17 again depicts an example of an electronic interface 1720 of package 1610 in the form of a connection tab, and an electronic interface 1722 of communication hub 1620 in the form of a connection port formed by one or both of recessed regions 1710 and 1714 of portions 1622 and 1624, respectively. Electronic interfaces 1720 and 1722 each include a set of pins, such as previously described with reference to FIGS. 12 and 13, for example. In at least some implementations, a second pair of electronic interfaces may be provided at an opposite side of the connection tab from electronic interface 1720 and at portion 1624 of the communication hub. Furthermore, in at least some implementations, an intermediate conductive layer may be disposed between electronic interfaces 1720 and 1722 as will be described in further detail with reference to FIG. 18.

FIG. 17 further depicts examples of alignment structures in the form of an alignment post or protrusion 1716 provided on portion 1624 of communication hub 1620, and an alignment port or opening 1718 formed within package 1610 that accommodates post 1716. Additionally, portion 1622 includes an alignment port or opening 1712 that accommodates a terminal end of post 1716 that passes through port 1718 of package 1610 to further secure and align portions 1622 and 1624 with the package. In contrast to the example depicted in FIG. 15, FIG. 17 depicts an example in which alignment port 1718 formed in package 1610 passes through cover 1612 but not through tray 1614 to secure and align the package to communication hub 1620.

While not depicted in FIGS. 14-17, in at least some implementations, an intermediate layer may be disposed between the cover and the tray that includes or otherwise defines respective openings in the layer that correspond to the compartments of the tray. The intermediate layer may enable alignment of perforations and/or electrical contacts in the cover with the compartments of the tray during assembly or manufacturing of the packaging system. As an example, the cover and intermediate layer may be pre-assembled prior to adhering or otherwise joining the tray to the intermediate layer. The intermediate layer may correspond to or be co-extensive with the exterior boundaries of the tray and/or the cover, depending on implementation. The intermediate layer may include an interface and/or alignment structures to interface with an electronic module, such as previously described with reference to the tray. Furthermore, alignment structures of the electronic module and/or tray may pass through openings formed in the intermediate layer to provide alignment and retention of the intermediate layer in relation to the electronic module and/or tray. An adhesive may be used to join tray to cover, intermediate layer to tray, and/or intermediate layer to cover.

Figure 18:
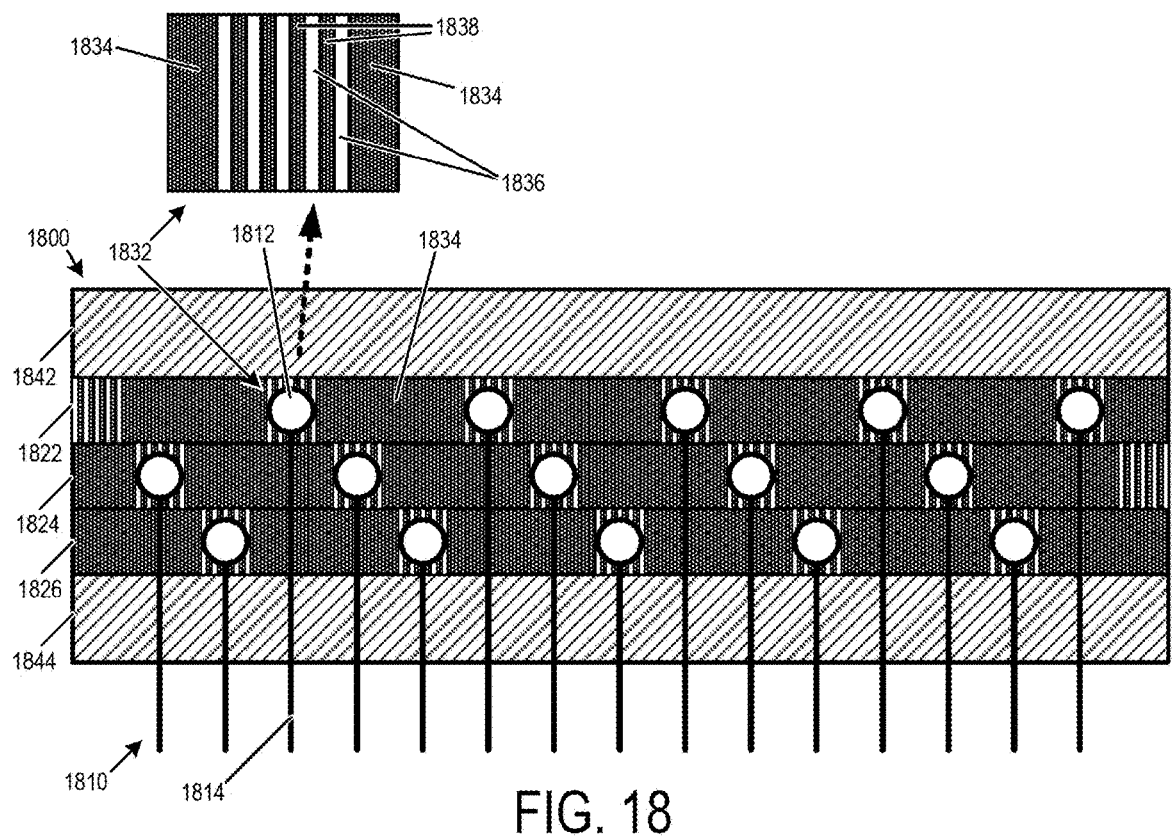
FIG. 18 depicts an example intermediate layer that may be disposed between two electronic interfaces.

FIG. 18 depicts an example of an intermediate conductive layer 1800 that may be disposed between two electronic interfaces, such as an electronic interface of a sensor-enabled package and an electronic interface of a communication hub. Within FIG. 18, a first set of electrically conductive pins 1810 (or other suitable electrically conductive structure) and associated electrically conductive traces or paths of a first electronic interface are depicted in relation to conductive layer 1800 of which pin 1812 and associated trace 1814 are an example. A second set of electrically conductive pins and associated electrically conductive traces or paths of a second electronic interface may reside on an opposite side of conductive layer 1800, not depicted in FIG. 18.

Layer 1800 includes a plurality of segments such as 1822, 1824, 1826, etc. As previously described with reference to FIG. 7, a set of electrically conductive pins may be arranged in a plurality of rows. FIG. 18 depicts an example in which each segment of conductive layer 1800 is associated with a row of electrically conductive pins. For example, segment 1822 may be in physical and electrical contact with pin 1812 and other pins of its row. Segments 1824 and 1826 may be likewise in physical and electrical contact with pins of other rows. While conductive layer 1800 includes three segments, it will be understood that a conductive layer may include other suitable quantities of segments one, two, four or more segments, each of which may correspond to one or more electrically conductive pins of an electronic interface.

Each of segments 1822, 1824, 1826, etc. may include one or more electrically conductive regions of which region 1832 is an example, and one or more electrically insulated regions (i.e., electrically non-conductive regions. FIG. 18 further depicts an expanded view of an example electrically conductive region 1832 with pin 1812 removed to provide a view of the underlying structure of segment 1822. Each electrically conductive region may be formed from a set of one or more electrically conductive sub-segments, and is bordered on either side by electrically insulated subsegments 1834 as examples of electrically insulated regions. In this example, electrically conductive region 1832 includes a plurality of electrically conductive sub-segments 1836 that are interleaved with electrically insulated subsegments 1838. Each pin may contact its respective electrically conductive region via a plurality of electrically conductive subsegments 1836, however, contact with only a single electrically conductive subsequent may be required to establish electrical contact with features located on an opposite side of layer 1800. Electrically insulated subsegments 1838 of electrically conductive region 1832 are each of a narrower width as compared to electrically insulated regions 1834 that flank each side of the electrically conductive region, as measured along a long axis of each segment. The greater width of electrically insulated subsegments 1834 provides an insulated region across which electrically conductive traces or paths may be routed to insulate those electrically conductive features from electrically conductive features located on an opposite side of layer 1800. For example, trace 1814 may be routed over electrically insulated regions of segments 1824 and 1826.

In at least some implementations, segments 1822-1826 may be formed be formed from a compressible and/or elastomeric material. As anon-limiting example, electrically conductive subsegments 1836 may be formed from a silver-filled conductive silicone to provide a compressible/elastomeric conductor; however other suitable conductive materials may be used, such as gold, copper, etc. Electrically insulated regions 1834 and/or electrically insulated subsegments 1838 may be formed from a compressible and/or elastomeric material, such as a silicone rubber, for example.

Layer 1800 may include edge segments 1842 and/or 1844 that surround one or both sides of segments 1822-1826, etc. Each edge segment may take the form of an electrical insulator and may support interior segments 1822-1826, particularly where the electrically insulated regions or subsegments of the interior segments include or are formed from a compressible material. Edge segments 1842 and 1844 may take the form of a compressible, elastomeric insulator in at least some implementations. For example, edge segments 1842 and 1844 may be formed from a silicone rubber.

Figure 19:
FIG. 19 depicts an example of an alternative segment configuration of an intermediate layer.

FIG. 19 depicts an alternative configuration of a segment 1910 that may be used in place of some or all of the segments 1824-1826 of layer 1800, depending on implementation and pin/trace configuration. In FIG. 19, segment 1910 includes a repeating pattern of electrically conductive subsegments 1912 interleaved with electrically insulated subsegments 1914. Subsegments 1912 may be of the same or different width (e.g., wider or narrower) than subsegments 1914, again depending on implementation. A potential disadvantage of segment 1910 as compared to segments 1824-1826 is that traces or other electrically conductive features routed over neighboring segments may be in electrical contact with the electrically conductive subsegments of those neighboring segments and therefore in electrical contact with any electrically conductive features located on an opposite side of the layer for those neighboring segments. Segment 1910 may be compressible and/or elastomeric in at least some implementations. As a non-limiting example, segment 1910 may take the form of a ZEBRA™ brand elastomeric connector manufactured by FUJIPOLY™.

Figure 20:
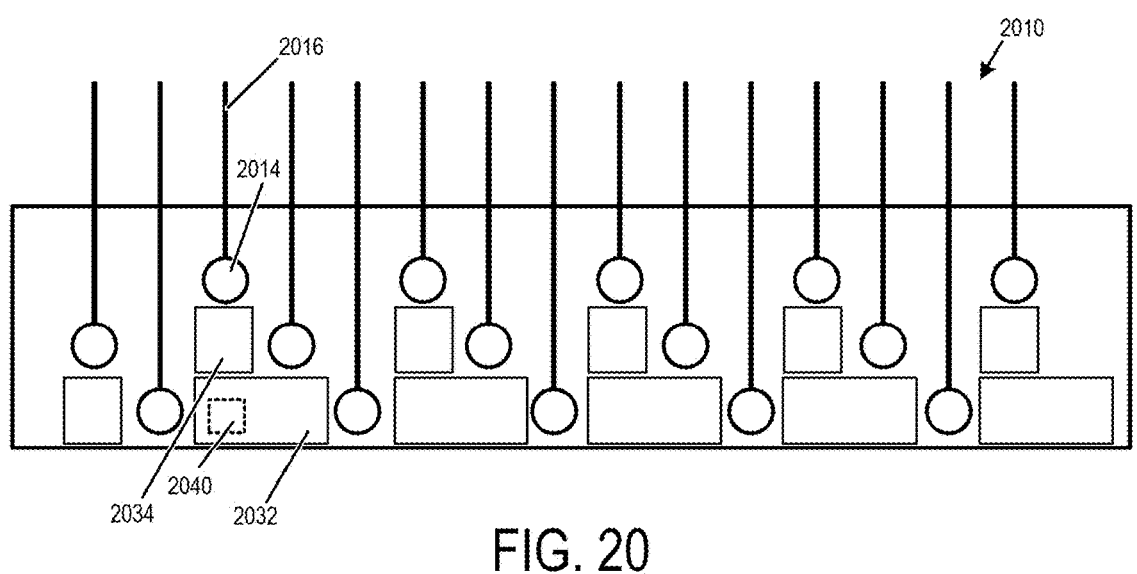
FIG. 20 depicts an example electronic interface.

FIG. 20 depicts an example of an electronic interface 2010 that may reside on opposite side of layer 1800 depicted in FIG. 18. In FIG. 20, electronic interface 2010 is viewed from the side of layer 1800 in the same perspective as FIG. 18 with the layer and the set of pins 1810 and associated traces removed. Electronic interface 2010 includes a set of electrically conductive pins and associated electrically conductive traces of which pin 2014 and trace 2016 are examples.

FIG. 20 further depicts example regions 2032, 2034, etc. that are insulated from features of an opposing electronic interface by electrically insulated regions or subsegments of layer 1800. If segment 1910 of FIG. 19 is instead used in place of one or more of segments 1822-1826, regions 2032, 2034, etc. may take the form of insulator layers that electrically insulate electronic features (e.g., 2040) of electronic interface 2010 from electrically conductive subsegments 1912 of segment 1910 as well as electronic features of the opposite electronic interface of the layer, such as depicted in FIG. 18. In an alternative configuration, regions 2032, 2034, etc. may take the form of electrical conductors that functionally preclude the use of segment 1910 or other segments that do not have a specific configuration (e.g., pattern/shape/size) of insulator/conductor subsegments, such as the configuration depicted for segments 1822-1826 of layer 1800.

While the preceding examples include electronic interfaces having one or more rows of electrically conductive pins having a linear arrangement, in other examples a set of electrically conductive pins may have a non-linear arrangement in at least two dimensions, such as an arc, a circle or ellipse, a polygon, or a portion thereof. For example, a sensor enabled package may have an arrangement of containers surrounding an interior region within which a communication hub may be coupled. In this example, the pins of the package may surround some or all of this interior region, and the communication hub may have corresponding pins located along some or all of the exterior edges of the hub to interface with the pins of the package. Accordingly, it will be understood that the pin configurations disclosed herein should be considered non-limiting, as various other configurations may be used.

Figure 21:
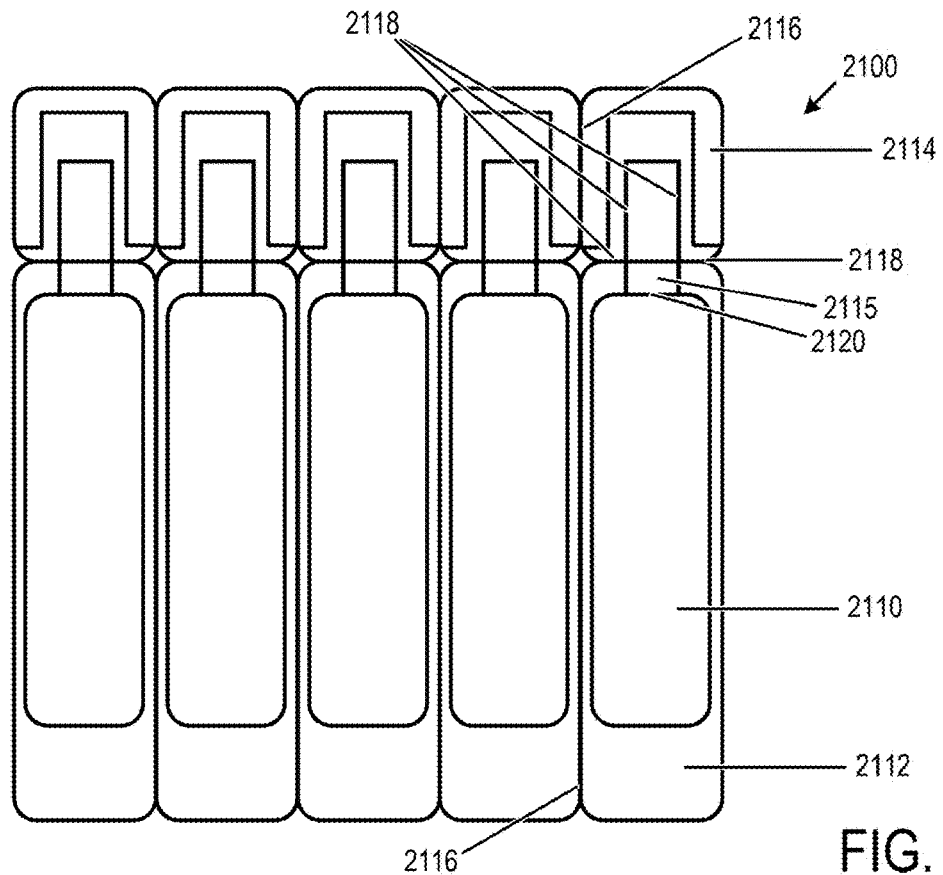
FIGS. 21 and 22 depict an example of pharmaceutical packaging combined with an intelligent usage NFC label.
Figure 22:
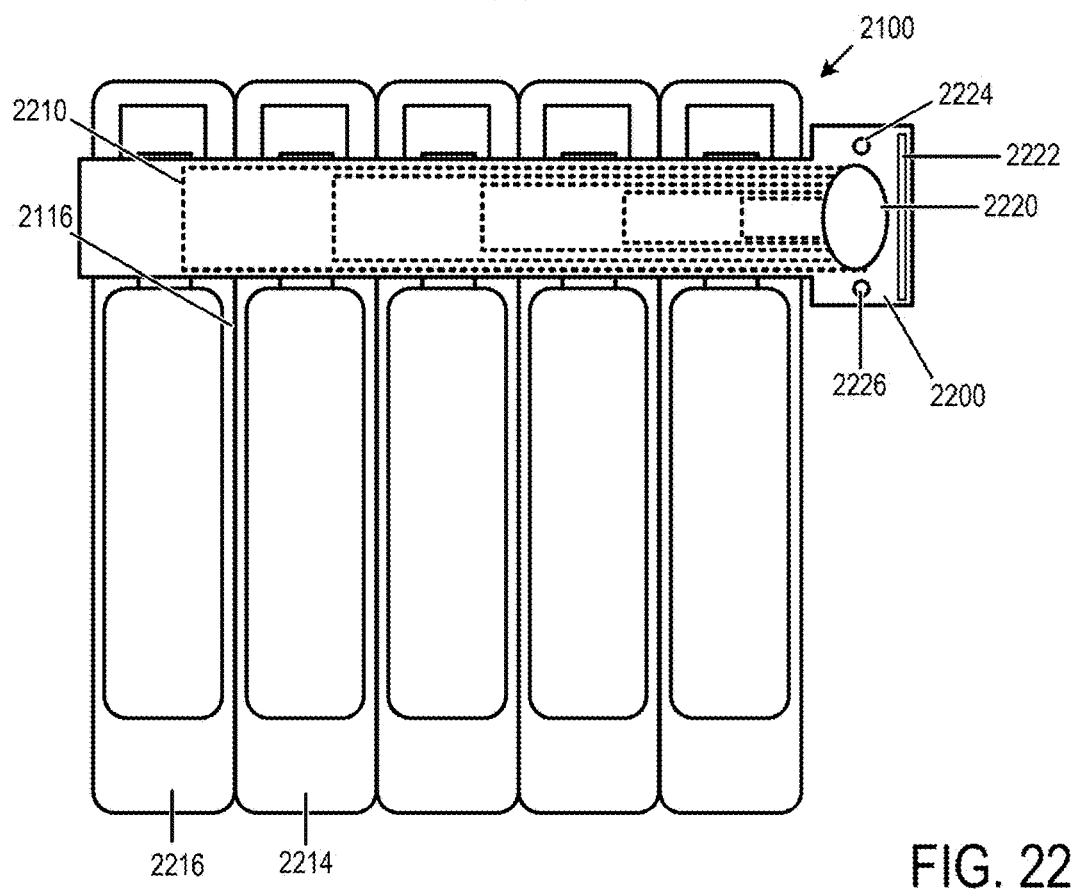

FIGS. 21 and 22 depict an example of pharmaceutical packaging 2100 combined with an intelligent usage NFC label 2200 to form a packaging system. In FIG. 21, pharmaceutical packaging 2100 is depicted without NFC label 2200, to provide a view of the upper portion of the packaging that is covered by the NFC label in FIG. 22. The pharmaceutical packaging in this example includes a set of multiple vials (e.g., five vials in this example) each containing a liquid pharmaceutical product, of which vial 2110 is an example. The vials of packaging 2100 are non-limiting examples of compartments that are formed by respective package portions 2112. Accordingly, each vial is associated with a respective package portion that forms a modular unit. Each package portion further includes a removeable cap portion 2114. Modular units are joined to each other by a boundary (e.g., perforation, scalloped/thin-walled region, or other suitable structure) that enables a modular unit to be removed from another modular unit of the set. In this example, boundary 2116 spans the entirety of packaging 2100 from a first side to a second side. Removable cap portion 2114 may be joined to vial 2110 via a boundary 2118 (e.g., perforation, scalloped/thin-walled region, or other suitable structure) that enables the cap portion to be removed from the vial. In this example, boundary 2118 spans an entire width of modular unit 2112 from a first side to a second side of the modular unit. In at least some implementations, upon removal of cap portion 2114 from vial 2110, a neck of the vial may be opened enabling liquid within the vial to be accessed via a syringe or poured from the vial through a neck region 2115. However, in at least some implementations, vial 2110 may include a thin-walled seal 2120 along a pathway of the neck of the vial that precludes pouring of the liquid from the vial, while also allowing a syringe inserted into the neck of the vial to penetrate the seal to gain access to the liquid contents of the vial. In each of these implementations, an exterior of vial 2110 may be formed from a thicker wall that precludes or makes it more difficult for syringe to penetrate the vial, as compared to seal 2120.

FIG. 22 depicts the NFC label 2200 applied to or integrated with pharmaceutical packaging 2100. NFC label 2200 includes a set of electrically conductive pathways of which pathway 2210 is an example. Each modular unit of the packaging may be associated with at least one pathway to enable detection of a breach of at least one of boundaries 2116 and/or 2118 associated with the modular unit. In this example, pathway 2210 spans boundary 2116 between modular unit 2214 and 2216. Upon removal of modular unit 2216 from modular unit 2214, pathway 2210 may be broken, which may be detected by a logic subsystem of NFC chip 2220, as previously described herein. Additionally or alternatively, each pathway (e.g., pathway 2210) spans boundary 2118 between each cap portion and its vial portion. Accordingly, electrically conductive pathways may span boundaries between a vial and a cap portion of each modular unit, enabling removal of the cap portion from the vial to be detected by a logic subsystem of NFC chip 2220. It will be appreciated that NFC chip 2220 may alternatively or additionally take the form of any of the previously described electronic module components disclosed herein that may reside on-board product packaging, and may omit wireless communications capabilties. NFC label 2200 may include an interface 2222 (e.g., including a pin-out pattern that includes terminal ends of electrically conductive pathways), such as the previously described electronic interfaces disclosed herein that enable the NFC label 2200 to be joined with an electronic module (e.g., the communication module disclosed herein). In this implementation, interface 2222 may include one or more electronic pins or contacts and/or alignment structures (e.g., 2224, 2226), such as previously described with reference to FIGS. 12-17, for example.

Figure 23:
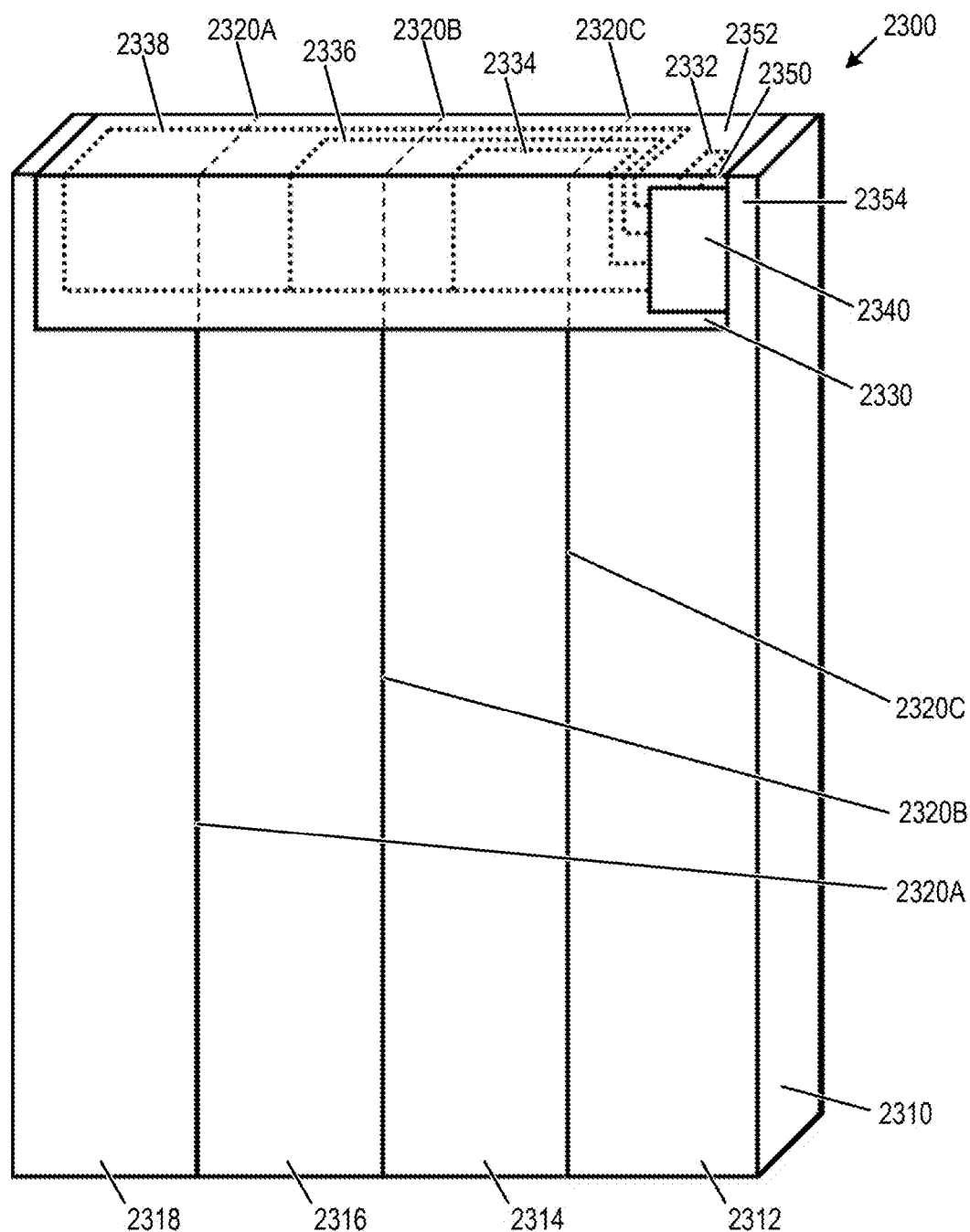
FIG. 23 depicts another example of a packaging system.

FIG. 23 depicts an example of a packaging system 2300 that includes a package 2310 and a film portion 2330. Package 2310 includes a set of multiple package portions 2312, 2314, 2316, 2318, etc. that each form a discrete compartment. The multiple package portions join each other and are separable from each other along one or more boundaries, including 2320A, 2320B, 2320C, etc. Film portion 2330 interfaces with the package and spans the one or more boundaries 2320. In an example, film portion 2330 may be applied or otherwise adhered to package 2310 by an adhesive or other suitable technique, which for example, enables the disclosed film portion to be utilized in combination with packages obtained from third-party sources by a downstream party. Film portion 2330 may include perforations, scalloped regions, and/or thinner cross-sections along boundaries 2320A, 2320B, 2320C, etc. to assist in tearing or separating the film portion along such boundaries. Furthermore, in at least some examples, packaging system 2300 may include a communication module 2340 mounted to at least one of the package or the film portion. In the example depicted in FIG. 23, communication module 2340 is mounted to film portion 2330. Communication module 2340 includes a logic subsystem, a wireless transmitter, and/or other suitable electronic components described herein. Alternatively, communication module 2340 may instead take the form of an interface region that includes a pin-out pattern and/or alignment ports to be electrically coupled with a communication module.

Film portion 2330 includes a set of one or more electrically conductive traces 2334, 2336, 2338, etc. that each span a respective boundary of the one or more boundaries. For example, electrically conductive trace 2338 spans boundary 2320A between package portions 2318 and 2316, electrically conductive trace 2336 spans boundary 2320B between package portions 2316 and 2314, and electrically conductive trace 2334 spans boundary 2320C between package portions 2314 and 2312. In the example depicted in FIG. 23, each electrically conductive trace of the set of electrically conductive traces forms a respective circuit loop that has a terminal end that terminates at communication module 2340. The logic subsystem of communication module 2340 may be programmed with instructions executable by the logic subsystem to: measure, via the terminal ends of the set of electrically conductive traces, an electrical property (e.g., one or more of a voltage, current, power, resistance, capacitance, impedance, etc.) of each electrically conductive trace to determine a state of each boundary of the one or more boundaries, and transmit, via the wireless transmitter, communications to a remote wireless receiver indicating the state (e.g., broken or unbroken) of each boundary of the one or more boundaries. For example, as package portion 2318 is separated from package portion 2316 along boundary 2320A, a portion of electrically conductive trace 2338 that spans boundary 2320A may be broken, thereby changing an electrical property of electrically conductive trace 2338, thereby enabling the logic system to detect removal of package portion 2318 from the remaining package portions of package 2310. As package portion 2316 is separated from package portion 2314 along boundary 2320B, a portion of electrically conductive trace 2336 that spans boundary 2320B may be broken, thereby changing an electrical property of electrically conductive trace 2336. As package portion 2314 is separated from package portion 2312 along boundary 2320C, a portion of electrically conductive trace 2334 that spans boundary 2320C may be broken, thereby changing an electrical property of electrically conductive trace 2334. The last remaining package portion 2312 may include electrically conductive trace 2332 that spans a boundary 2350 between a compartment cover 2352 (e.g., door, cap, film, etc.) and remaining body 2354 of the package portion. The logic subsystem may determine a state (open or closed) of the compartment of package portion 2312 by measuring a change in an electrical property of electrically conductive trace 2332 due to the breaking of the trace along boundary 2350 caused by compartment cover 2352 being opened. The logic subsystem of communication module 2340 may be further programmed with instructions executable by the logic subsystem to transmit, via the wireless transmitter, communications to a remote wireless receiver indicating the state of boundary 2350. Furthermore, in at least some examples, the instructions are further executable by the logic subsystem to transmit a pack identifier associated with package 2310 via the wireless transmitter to the remote wireless receiver. The package identifier may be obtained by the logic subsystem using any of the techniques described herein.

In at least some implementations, the methods and processes described herein may be tied to a computing system of one or more computing devices. In particular, such methods and processes may be implemented as a computer-application program or service, an application-programming interface (API), a library, and/or other computer-program product.

Figure 24:
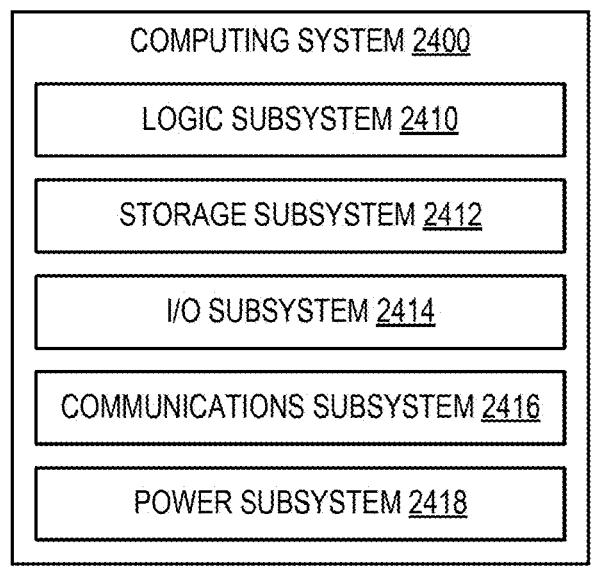
FIG. 24 depicts an example computing system.

FIG. 24 schematically shows a non-limiting example of a computing system 2400 that can enact one or more of the methods and processes described above. For example, computing system 2400 may be representative of components located on-board a sensor-enabled package, a communication hub/module, a packaging system, or the various computing devices and/or computing platforms disclosed herein. Computing system 2400 is shown in simplified form. Computing system 2400 may take the form of one or more personal computers, server computers, tablet computers, home-entertainment computers, network computing devices, gaming devices, mobile computing devices, mobile communication devices (e.g., smart phone), Internet of Things (IoT) devices, sensor-enabled packages, communication hubs/modules, packaging systems, and/or other computing devices.

Computing system 2400 includes a logic subsystem 2410 and a data storage subsystem 2412. Computing system 2400 may optionally include an input/output subsystem 2414, a communications subsystem 2416, a power subsystem 2418, and/or other components not shown in FIG. 24.

Logic subsystem 2410 includes one or more physical devices or machines configured to execute instructions. For example, the logic subsystem may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic subsystem may include one or more processors configured to execute software instructions. Additionally or alternatively, the logic subsystem may include one or more hardware or firmware logic subsystems configured to execute hardware or firmware instructions. Processors of the logic subsystem may be single-core or multi-core, and the instructions executed thereon may be configured for sequential, parallel, and/or distributed processing. Individual components of the logic subsystem optionally may be distributed among two or more separate devices, which may be remotely located and/or configured for coordinated processing. Aspects of the logic subsystem may be virtualized and executed by remotely accessible, networked computing devices configured in a cloud-computing configuration.

Storage subsystem 2412 includes one or more physical devices or machines configured to hold instructions executable by the logic subsystem to implement the methods and processes described herein. When such methods and processes are implemented, the state of storage subsystem 2412 may be transformed—e.g., to hold different data. Data stored by storage subsystem 2412 may include pin-out profiles, states (e.g., opened/closed/broken/unbroken, etc.) determined with respect to individual compartments, identifiers, timestamps, and other suitable data disclosed herein. In at least some examples, the pin-out profile may specify, for a package ID, the relative location and/or size of a compartment within the package (e.g., a compartment ID) and/or the contents (e.g., medication type, ancillary type, quantity, size, etc.) of the compartment with which a particular pin or set of pins are used to determine the state of that compartment, thereby enabling a computing system to determine and report whether a particular compartment of particular contents has been accessed. The pin-out profile may further indicate a quantity of active pins of the package and/or a relative positioning of those pins of the package, thereby enabling a communications module that interfaces with the package to determine which pins correspond to which functions. Additional pins may be provided that provide other suitable functions, including temperature sensing, conveying electrical power, etc.

Storage subsystem 2412 may include removable and/or built-in devices. Storage subsystem 2412 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage subsystem 2412 may include volatile, nonvolatile, dynamic, static, read/write, read-only, random-access, sequential-access, location-addressable, file-addressable, and/or content-addressable devices.

It will be appreciated that storage subsystem 2412 includes one or more physical devices or machines. However, aspects of the instructions described herein alternatively may be propagated by a communication medium (e.g., an electromagnetic signal, an optical signal, etc.) that is not held by a physical device for a finite duration. Furthermore, aspects of instructions described herein may reside on removable media devices, such as represented schematically at 2422.

Logic subsystem 2410 and storage subsystem 2412 may be collectively referred to as a computing platform. Aspects of logic subsystem 2410 and storage subsystem 2412 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "program" and "engine" may be used to describe an aspect of computing system 2400 implemented to perform a particular function. In some cases, a program or engine may be instantiated via logic subsystem 2410 executing instructions held by storage subsystem 2412. It will be understood that different programs and/or engines may be instantiated from the same application, service, code block, object, library, routine, API, function, etc. Likewise, the same program and/or engine may be instantiated by different applications, services, code blocks, objects, routines, APIs, functions, etc. The terms "program" and "engine" may encompass individual or groups of executable files, data files, libraries, drivers, scripts, database records, etc.

It will be appreciated that a "service", as used herein, may refer to an application program executable across multiple user sessions. A service may be available to one or more system components, programs, and/or other services. In some implementations, a service may run on one or more server-computing devices.

When included, input/output subsystem 2414 may comprise or interface with one or more input devices and/or output devices such as a sensor, keyboard, mouse, touch screen or pad, game controller, microphone, graphical display, illumination device, audio speaker, haptic feedback device (e.g., vibration motor), etc. These input/output devices may form part of or may be peripheral to computing system 2400, and may communicate with I/O subsystem 2414 via a wired or wireless link, depending on implementation. I/O subsystem 2414 may include electronic components used by logic subsystem 2410 to measure an electrical property of electrically conductive pathways of the packaging systems disclosed herein, including voltage meters, amp meters, power sources, analog to digital converters, etc.

When included, communication subsystem 2416 may be configured to communicatively couple computing system 2400 with one or more other computing devices or computing systems. Communication subsystem may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 2400 to send and/or receive messages to and/or from other devices via a network such as the Internet.

Power subsystem 2418 may include one or more energy storage devices, such as a battery to power computing system 2400 in a mobile implementation. Alternatively or additionally, power subsystem 2418 may include an interface over which power may be received from a remote source via a wired or wireless link.

In view of the various package configurations disclosed herein, an example packaging system comprises: a package forming a set of discrete compartments; and a film portion interfacing with the package, the film portion including a set of one or more electrically conductive traces in which each electrically conductive trace is associated with a respective compartment of the set of discrete compartments. In an example, one or more electrically conductive traces may be associated with a set of two or more compartments that have related contents. For example, in the case of an epilepsy treatment package, each peel-off portion forming a cover of the compartments reveals both a pill compartment and a compartment for a pre-dosed oral syringe. Accordingly, it will be appreciated that two or more compartments may be monitored as a set using a common electrically conductive trace. Each electrically conductive trace of the set of electrically conductive traces forming a respective circuit loop that has a terminal end that terminates within an interface region of the film portion to collectively form a termination pattern. In at least some examples, each circuit loop may have two terminal ends located at each end of the loop that terminate within the interface region. At least one of the package or the film portion having one, two or more alignment ports defined therein that are arranged according to an alignment pattern, each alignment port passing through at least one of the package or film portion. In this or any other example disclosed herein, the packaging system further comprises a communication module, including: a module body having one, two or more alignment posts arranged according to the alignment pattern in which each alignment post passes through an alignment port; and electronic components mounted to the module body. The electronic components may include: a set of electrical contacts arranged in a contact pattern in which the termination pattern corresponds to at least a portion of the contact pattern of the set of electrical contacts so that each terminal end of the termination pattern interfaces with a corresponding electrical contact of the communication module, a wireless transmitter, and a logic subsystem programmed with instructions executable by the logic subsystem to: measure, via electrical contacts interfacing with the terminal ends, an electrical property of each electrically conductive trace that is associated with each compartment of the set of discrete compartments to determine an compartment state of that compartment, and transmit wireless communications indicating the compartment state of each compartment of the set of discrete compartments to a remote wireless receiver. In this or any other example disclosed herein, the module body is formed from a first body portion and a second body portion; and the one, two or more alignment posts are formed on the first body portion, pass through the one, two or more alignment ports, and are secured to the second body portion to retain the interface region between the first body portion and the second body portion. In this or any other example disclosed herein, the one, two or more alignment ports are located on opposite sides of the interface region. In this or any other example disclosed herein, the package or the film portion further includes an electronic component storing a pack identifier. In this or any other example disclosed herein, the logic subsystem is further programmed to: receive the pack identifier from the electronic component of the package or the film portion; retrieve a pin-out profile (e.g., from a computer-readable storage device) for the interface region based on the pack identifier; and associate each electrical contact of the set of electrical contacts with a corresponding function identifier (e.g., identifying the function of the pin, such as measuring a state (e.g., open or closed; or broken or unbroken) associated with a particular compartment based on the pin-out profile. In this or any other example disclosed herein, the logic subsystem is further programmed to: receive the pack identifier from the electronic component; and transmit, via the wireless transmitter, the pack identifier to the remote wireless receiver. In this or any other example disclosed herein, the packaging system further comprises: a remote computing system (e.g., a server system or other suitable computing device) communicatively coupled to the remote wireless receiver, and configured to: receive the pack identifier transmitted by the logic subsystem; retrieve a pin-out profile for the interface region based on the pack identifier; and associate each electrical contact of the set of electrical contacts with a corresponding function identifier based on the pin-out profile. In this or any other example disclosed herein, the pack identifier is received from the electrical component of the package or the film portion via an electrical contact of the set of electrical contacts. In this or any other example disclosed herein, the pack identifier is received from the electrical component of the package or film portion via a near-field wireless link. In this or any other example disclosed herein, the electrical component of the package or film portion includes a computer-readable memory device and a near-field wireless transmitter to transmit the pack identifier; and the electronic components of the communication module include a near-field wireless receiver by which the pack identifier is received from the near-field wireless transmitter. In this or any other example disclosed herein, the package includes a tray having a set of depressions formed therein with respect to an interior-facing surface of the tray; and the film portion includes a backing film interfacing with the interior-facing surface of the tray and enclosing the set of depressions to form the set of discrete compartments. In this or any other example disclosed herein, each electrically conductive trace is associated with a respective compartment by spanning a respective depression of the tray that forms that compartment. In this or any other example disclosed herein, the tray and the backing film form a blister pack. In this or any other example disclosed herein, the packaging system further comprises an intermediate layer disposed between at least a portion of the tray and at least a portion of the backing film, the intermediate layer having a set of openings formed therein that correspond to the set of depressions formed in the tray to enable access between the interior-facing surface of the depressions and an interior-facing surface of the backing film through the intermediate layer. In this or any other example disclosed herein, each alignment port of the one, two or more alignment ports further pass through the intermediate layer. In this or any other example disclosed herein, the package includes a set of multiple package portions that each form a respective compartment of the set of discrete compartments, the multiple package portions joining each other and being separable from each other along one or more boundaries; the set of one or more electrically conductive traces each span a respective boundary of the one or more boundaries; and each electrically conductive trace is associated with a respective compartment by spanning a respective boundary of a package portion that forms that compartment. In this or any other example disclosed herein, the interface region is located along an exterior edge of the film portion.

According to another example of the present disclosure, a packaging system comprises a blister pack, including: a tray having a set of depressions formed therein with respect to an interior-facing surface of the tray; a backing film interfacing with the interior-facing surface of the tray and enclosing the set of depressions to form a set of discrete compartments, wherein: the backing film includes a set of electrically conductive traces in which at least one electrically conductive trace is associated with each discrete compartment to enable electronic monitoring of an compartment state of that discrete compartment, the set of electrically conductive traces terminating within an interface region of the backing film in which each electrical conductive trace has a corresponding terminal end, the terminal ends of the set of electrically conductive traces collectively forming a termination pattern within the interface region; the blister pack having two or more alignment ports defined therein arranged in an alignment pattern, each alignment port passing through at least one of the tray and/or the backing film. The packaging system may further comprise: a communication module operable with the blister pack, the communication module including: a module body having two or more alignment posts arranged in the alignment pattern in which each alignment post passes through an alignment port of the blister pack; electronic components mounted to the module body, including: a set of electrical contacts arranged in a contact pattern in which the termination pattern of the blister pack corresponds to at least a portion of the contact pattern of the set of electrical contacts so that each terminal end of the termination pattern interfaces with a corresponding electrical contact of the communication module; a logic subsystem programmed with instructions executable by the logic subsystem to measure, via electrical contacts interfacing with the terminal ends, an electrical property of each electrically conductive trace that is associated with each discrete compartment to enable the electronic monitoring of the compartment state of that discrete compartment; and a wireless transmitter to transmit wireless communications from the logic subsystem to a remote wireless receiver. The module body may be formed from a first body portion and a second body portion; and the two or more alignment posts may be formed on the first body portion, pass through the two or more alignment ports of the blister pack, and are secured to the second body portion to retain the interface region of the blister pack between the first body portion and the second body portion. The two or more alignment ports may be located on opposite sides of the interface region of the blister pack. The blister pack may further include a pack identifier; and the logic subsystem may be further programmed to: receive the pack identifier from the blister pack; retrieve a pin-out profile for the blister pack based on the pack identifier; and associate each electrical contact of the set of electrical contacts with a corresponding function identifier based on the pin-out profile. The blister pack may further include: an intermediate layer disposed between at least a portion of the tray and at least a portion of the backing film, the intermediate layer having a set of openings formed therein that correspond to the set of depressions formed in the tray to enable access between the interior-facing surface of the depressions and an interior-facing surface of the backing film through the intermediate layer. Each alignment port of the two or more alignment ports may further pass through the intermediate layer.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A packaging system, comprising:
a communication module, including:
  a module body; and
  electronic components mounted to the module body, the electronic components including:
    a module-side set of electrical contacts arranged in a contact pattern configured to interface with a second set of electrical contacts of a sensor-based accessory;
    a wireless transmitter, and
    a logic subsystem programmed with instructions executable by the logic subsystem to:
      receive an identifier of an electronic component of the accessory;
      retrieve a pin-out profile for the second set of electrical contacts of the accessory based on the identifier;

associate each electrical contact of the second set of electrical contacts with a corresponding function identifier of a sensor of the accessory based on the pin-out profile;
measure a state of the accessory, via the module-side set of electrical contacts interfacing with the second set of electrical contacts of the accessory, based on an electrical property of one or more of the second set of electrical contacts for one or more of the function identifiers; and
transmit wireless communications indicating the state to a remote computing system via the wireless transmitter.

2. The packaging system of claim 1, wherein the accessory is removable from the communication module.

3. The packaging system of claim 2, wherein the module body has two or more alignment posts arranged according to an alignment pattern in which each alignment post passes through an alignment port formed in an accessory body of the accessory.

4. The packaging system of claim 3, wherein the module body is formed from a first body portion and a second body portion; and
wherein the two or more alignment posts are formed on the first body portion, pass through the two or more alignment ports, and are secured to the second body portion.

5. The packaging system of claim 3, wherein the two or more alignment posts are located on opposite sides of the module-side set of electrical contacts.

6. The packaging system of claim 1, wherein the state of the accessory includes a compartment-breach state of each compartment of a set of discrete compartments of the accessory.

7. The packaging system of claim 1, wherein the state of the accessory includes a temperature state, an air temperature state, a humidity state, a light state, a battery state, a blood-pressure state, or a filter state.

8. The packaging system of claim 1, wherein the logic subsystem is further programmed to:
transmit wireless communications indicating the identifier to the remote computing system via the wireless transmitter.

9. The packaging system of claim 1, wherein the pin-out profile is retrieved from the remote computing system.

10. The packaging system of claim 1, wherein the identifier is received via the module-side set of electrical contacts or at a wireless receiver of the communication module via a near-field wireless link.

11. The packaging system of claim 1, further comprising the accessory.

12. A mobile computing system, comprising:
a logic subsystem; and
a data storage subsystem having instructions stored thereon executable by the logic subsystem to:
receive an identifier of an electronic component of a sensor-based accessory;
retrieve a pin-out profile for a set of electrical contacts of the accessory based on the identifier;
associate each electrical contact of the set of electrical contacts with a corresponding function identifier of a sensor of the accessory based on the pin-out profile;
measure a state of the accessory based on an electrical property of one or more of the set of electrical contacts for one or more of the function identifiers; and
transmit wireless communications indicating the state to a remote computing system via a wireless transmitter.

13. The mobile computing system of claim 12, wherein the accessory is removable from the mobile computing system.

14. The mobile computing system of claim 13, wherein the mobile computing system has two or more alignment posts arranged according to an alignment pattern in which each alignment post passes through an alignment port formed in an accessory body of the accessory.

15. The mobile computing system of claim 12, wherein the state of the accessory includes a compartment-breach state of each compartment of a set of discrete compartments of the accessory.

16. The mobile computing system of claim 12, wherein the state of the accessory includes a temperature state, an air temperature state, a humidity state, a light state, a battery state, a blood-pressure state, or a filter state.

17. The mobile computing system of claim 12, wherein the logic subsystem is further programmed to:
transmit wireless communications indicating the identifier to the remote computing system via the wireless transmitter.

18. The mobile computing system of claim 12, wherein the pin-out profile is retrieved from the remote computing system.

19. The mobile computing system of claim 12, wherein the identifier is received via the set of electrical contacts or at a wireless receiver via a near-field wireless link.

20. A method performed by a mobile computing system, the method comprising:
receiving an identifier of an electronic component of a sensor-based accessory;
retrieving a pin-out profile for a set of electrical contacts of the accessory based on the identifier;
associating each electrical contact of the set of electrical contacts with a corresponding function identifier of a sensor of the accessory based on the pin-out profile;
measuring a state of the accessory based on an electrical property of one or more of the set of electrical contacts for one or more of the function identifiers; and
transmitting wireless communications indicating the state to a remote computing system via a wireless transmitter.

* * * * *